United States Patent
Shimizu et al.

(10) Patent No.: US 8,822,671 B2
(45) Date of Patent: Sep. 2, 2014

(54) 2'-O-MODIFIED RNA

(75) Inventors: Mamoru Shimizu, Okinawa (JP); Takeshi Wada, Tokyo (JP); Kouichiro Arai, Tokyo (JP)

(73) Assignees: The University of Tokyo, Tokyo (JP); Chiralgen, Ltd., Okinawa (JP)

( * ) Notice: Subject to any disclaimer, the term of this patent is extended or adjusted under 35 U.S.C. 154(b) by 0 days.

(21) Appl. No.: 13/990,441

(22) PCT Filed: Nov. 28, 2011

(86) PCT No.: PCT/JP2011/077313
§ 371 (c)(1),
(2), (4) Date: May 30, 2013

(87) PCT Pub. No.: WO2012/073857
PCT Pub. Date: Jun. 7, 2012

(65) Prior Publication Data
US 2013/0253178 A1 Sep. 26, 2013

Related U.S. Application Data

(60) Provisional application No. 61/418,384, filed on Nov. 30, 2010.

(51) Int. Cl.
*C07H 21/02* (2006.01)
*C07H 19/10* (2006.01)
*C07H 23/00* (2006.01)
*C07H 19/06* (2006.01)
*C07H 1/00* (2006.01)
*C07H 19/067* (2006.01)
*C07H 19/167* (2006.01)

(52) U.S. Cl.
CPC .............. *C07H 21/02* (2013.01); *C07H 19/10* (2013.01); *C07H 23/00* (2013.01); *C07H 19/06* (2013.01); *C07H 1/00* (2013.01); *C07H 19/067* (2013.01); *C07H 19/167* (2013.01)
USPC ... 536/25.3; 536/25.31; 536/26.7; 536/26.71; 536/26.8

(58) Field of Classification Search
None
See application file for complete search history.

(56) References Cited

PUBLICATIONS

Pontiggia et al. Nucleic Acids Symposium Series No. 52 (2008), pp. 521-522.*
Supplementary European Search Report Issued in corresponding European Patent Application No. 11 84 4255 dated Apr. 7, 2014 (11 pages).
K. Arai et al; "Synthesis and Properties of Novel 2'-0-alkoxymethyl-modified Nucleic Acids"; Bioorganic & Medicinal Chemistry Letters, vol. 21, pp. 6285-6287; Sep. 11, 2011 (3 pages).
A. Kiviniemi et al; "Solid-Supported $2^1$-0-Glycoconjugation of Oligonucleotides by Azidation and Click Reactions"; Bioconjugate Chemistry, vol. 22, pp. 1249-1255; Jun. 15, 2011 (7 pages).
R. Pontiggia et al.; "DNAzymes and Ribozymes Carring 2'-C-methyl Nucleotides"; Nucleic Acids Symposium Series, No. 52, pp. 521-522; Sep. 11, 2008 (2 pages).
S. Yamakage et al; "1-(2-Chloroethoxy) Ethyl Group for the Protection of 2'-Hydroxyl Group in the Synthesis of Oligoribonucleotides"; Tetrahedron Letters, vol. 30, No. 46, pp. 6361-6364; Jan. 11, 1989 (4 pages).
X. Wu et al; "Synthesis of 5'-C- and 2'-0-(Bromoalkyl)-Substituted Ribonucleoside Phosphoramidites for the Post-synthetic Functionalization of Oligonucleotides on Solid Support"; Helvetica Chimica Acta, vol. 83, pp. 1127-1144; Jan. 1, 2000 (18 pages).
G.V. Bobkov et al; "Phosphoramidite Building Blocks for Efficient Incorporation of 2'-0-aminoethoxy(and propoxy) methyl Nucleosides Into Oligonucleotides"; Tetrahedron, vol. 64, No. 27, pp. 6238-6251; Jun. 30, 2008 (14 pages).
H. Saneyoshi et al; "A General Method for the Synthesis of 2'-O-Cyanoethylated Oligoribonucleotides Having Promising Hybridization Affinity for DNA and RNA and Enhanced Nuclease Resistance"; Journal of Organic Chemistry, vol. 70, No. 25, pp. 10453-10460; Jan. 1, 2005 (8 pages).
M. Egli et al; "Probing the Influence of Stereoelectronic Effects on the Biophysical Properties of Oligonucleotides: Comprehensive Analysis of the RNA Affinity, Nuclease Resistance, and Crystal Structure of Ten 2'-0-Ribonucleic Acid Modifications"; American Chemical Society, vol. 44, pp. 9045-9057, Jun. 28, 2005 (13 pages).

* cited by examiner

*Primary Examiner* — Patrick Lewis
(74) *Attorney, Agent, or Firm* — Osha Liang LLP

(57) ABSTRACT

A 2'-modified ribonucleoside having an alkoxymethyl protective group can be imparted with a high duplex-forming ability by introducing, as a substituent, a halogen atom into the protective group moiety. A modified form of RNA having a halogen-substituted alkoxymethyl protective group exhibits a high duplex-forming ability that is comparable to the duplex-forming ability of a 2'-O-methyl modified nucleic acid.

10 Claims, 3 Drawing Sheets

2'-O-MODIFIED RNA

TECHNICAL FIELD

The present invention relates to a 2'-O-modified RNA that is substituted with a halogen atom. More specifically, the invention relates to a 2'-O-alkoxymethyl-modified body of RNA that is substituted with a halogen atom, which has a high double strand-forming ability, and is easily manufactured, and a method of manufacturing the same.

BACKGROUND ART

In recent years, various nucleic acid analogs have been synthesized with an aim to use a nucleic acid molecule as a pharmaceutical or functional molecule. Among them, 2'-modified type nucleic acid exhibits improved double strand-forming ability and enzyme resistance by conducting an appropriate chemical modification, and is known to be a useful chemical modified-type nucleic acid.

Among the 2'-modified type nucleic acids, the 2'-O-methyl-modified body is the simplest 2'-O-alkyl type of the modified body. Non-Patent document 1 (Inoue, H; Miura, K.; Ohtsuka, E. et al, G *Nucleic Acid Res.*, 1987, 15, 6131-6148) suggests that 2'-O-methyl modification (O*—CH$_3$) of the nucleic acid can improve the $T_m$ value. On the other hand, Non-Patent Document 2 (Saneyoshi, H.; Seio, K.; Sekine, M., *J. Org. Chem.* 2005, 70, 10453-10460) describes that when 2'-O-Me modification is conducted at only one nucleic acid, the $T_m$ value decreases.

JP 2009-256335 A (Patent document 1 described below) discloses a method of manufacturing a ribonucleic acid that has an alkyl type-protective group at the 2' position.

In addition, Non-Patent Document 3 (Martin, P., *Helv. Chim. Acta.*, 1995, 78, 486-504) discloses a 2'-O-methoxyethyl-modified body (O*—C$_2$H$_4$OCH$_3$).

Most of the 2'-modified type RNAs including the 2'-O-methyl-modified body or the 2'-O-methoxyethyl-modified body mentioned above have a trouble in the introduction depending on the kind of the nucleic acid base. In other words, as for the 2'-O-methyl-modified body and the 2'-O-methoxyethyl-modified body, synthesis examples of only the RNA modified bodies having the pyrimidine nucleic acid base have been reported. In addition, it is necessary to search for an appropriate manufacturing method in which a synthesis method is changed depending on the kind of the nucleic acid base when these modified bodies are manufactured.

Non-Patent Document 4 (Tereshko, V.; Portmann, S.; Tay, E.; Martin, P; Natt, F.; Altmann, K.; Egli, M. *Biochemistry*, 1998, 37, 10626-10634) discloses a 2'-O-ethoxymethyl-modified body (O*—CH$_2$OC$_2$H$_5$). However, if the 2'-O-ethoxymethyl modification is performed, the double strand melting temperature is lowered. In other words, the 2'-O-ethoxymethyl-modified body has a low double strand-forming ability. For this reason, it has been considered that the 2'-O-ethoxymethyl-modified body is not useful as a modified body of RNA.

CITATION LIST

Patent Document

Patent document 1: Japanese Patent Document No. 2009-256335

Non-Patent Document

Non-Patent document 1: Inoue, H; Miura, K.; Ohtsuka, E. et al, G *Nucleic Acid Res.*, 1987, 15, 6131-6148

Non-Patent document 2: Saneyoshi, H.; Seio, K.; Sekine, M., *J. Org. Chem.* 2005, 70, 10453-10460

Non-Patent document 3: Martin, P., *Helv. Chim. Acta.*, 1995, 78, 486-504

Non-Patent document 4: Tereshko, V.; Portmann, S.; Tay, E.; Martin, P; Natt, F.; Altmann, K.; Egli, M. *Biochemistry*, 1998, 37, 10626-10634.

SUMMARY OF INVENTION

Technical Problem

An object of the invention is to manufacture a novel modified RNA that has a high double strand-forming ability.

Another object of the invention is to provide an effective method of manufacturing a modified RNA that can be adopted regardless of the nucleic acid base to be added.

Solution to Problem

The invention is basically based on the findings by Examples where a high double strand-forming ability can be imparted by introducing a halogen atom as a substituent into the moiety of the protective group of a modified body such as a ribonucleoside having an alkoxymethyl-based protective group. As described above, the modified body of RNA having the alkoxymethyl-based protective group has a low double strand-forming ability. However, the modified body of RNA having the halogen-substituted alkoxymethyl-based protective group of the invention exhibits a high double strand-forming ability that is comparable to the double strand-forming ability of the 2'-O-methyl-modified body of the nucleic acid.

In addition, the invention is based on the findings by Examples where the modified body of RNA can be easily synthesized regardless of the kind of the nucleic acid base of RNA by introducing a halogen atom as a substituent into the moiety of the protective group of a modified body such as a ribonucleoside having an alkoxymethyl skeleton. As described above, for the 2'-O-methyl-modified body or the 2'-O-methoxyethyl-modified body, an appropriate synthesis method has to be investigated depending on the nucleic acid base contained in the RNA, and there is a modified body that cannot be synthesized. On the other hand, in the manufacturing method of the invention, the 2'-modified body can be manufactured with a common method regardless of the nucleic acid base contained in the RNA. In other words, the manufacturing method of the invention can be said to a method that can easily synthesize the 2'-modified body having a high double strand-forming ability described above, regardless of the kind of the nucleic acid base in the RNA.

A first aspect of the invention relates to a ribonucleoside, a ribonucleotide, or a derivative thereof having a protective group at the 2'-position. When an oxygen atom at the 2'-position of the ribonucleoside, the ribonucleotide, or the derivative thereof is expressed as O*, the protective group is represented by the following Formula (I).

[Chemical Formula 1]

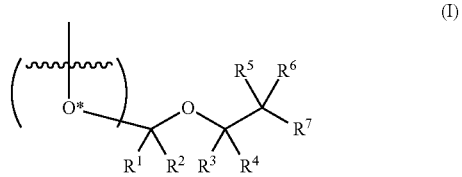

In the formula, O* represents an oxygen atom of a hydroxyl group at the 2' position of the ribonucleoside, the ribonucleotide, or the derivative thereof. Meanwhile, in Formula (I), the site connected to O* is the moiety of the protective group. For this reason, the moiety including the ribose and the nucleic acid base in Formula (I) is enclosed in the parentheses. The ribonucleotide is a unit constituting RNA. The ribonucleoside includes a ribose and a nucleic acid base. A ribonucleoside phosphate is a ribonucleotide. A derivative of the ribonucleoside or the ribonucleotide is those obtained by adding one or multiple substituents to the ribonucleoside or the ribonucleotide constituting RNA. Examples of the substituent include a $C_{1-3}$ alkyl group, or a $C_{1-3}$ haloalkyl group that substitutes a hydrogen atom of the ribonucleoside or ribonucleotide, but are not limited thereto.

In formula (I), R1 and R2 may be identical or different, and each represents a hydrogen atom, a C1-3alkyl group, a C2-3alkenyl group, a C2-3alkynyl group, a hydroxyC2-3alkyl group, or a C1-3haloalkyl group.

$R^3$ and $R^4$ may be identical or different, and each represents a hydrogen atom, a halogen atom, a $C_{1-3}$alkyl group, a $C_{2-3}$alkenyl group, a $C_{2-3}$alkynyl group, a hydroxy$C_{2-3}$alkyl group, or a $C_{1-3}$haloalkyl group.

R5 and R6 may be identical or different, and each represents a hydrogen atom, a halogen atom, a C1-3alkyl group, a C2-3alkenyl group, a C2-3alkynyl group, a hydroxyC2-3alkyl group, a C1-3haloalkyl group, a C1-3alkyl group substituted with one or two C6-12 aryl groups, or a C6-12aryl group optionally having a substituent. R7 represents a halogen atom or a C1-3haloalkyl group.

The C1-3alkyl group means a straight-chain alkyl group having one to three carbon atoms, a branched chain alkyl group having three carbon atoms, or a cyclic alkyl group having three carbon atoms. Examples of the straight-chain C1-3alkyl group include a methyl group, an ethyl group, or a propyl group. Examples of the branched chain C1-3alkyl group include an isopropyl group. Examples of the cyclic C1-3alkyl group include a cyclopropyl group. In the C1-3alkyl group, a straight-chain or branched chain group is preferred.

The C2-3alkenyl group means a straight-chain alkenyl group having two or three carbon atoms with at least one double bond, a branched chain alkenyl group having three carbon atoms, examples of which include a vinyl group, and an aryl group.

The C2-3alkynyl group means a straight-chain alkynyl group having two or three carbon atoms with at least one triple bond, examples of which include a 2-propynyl group.

The hydroxyC2-3alkyl group means a C2-3alkyl group substituted by at least one hydroxy group, examples of which include a 2-hydroxyethyl group, and a 3-hydroxypropyl group.

The C1-3haloalkyl group and a halogenoC1-3alkyl group are the same. The C1-3haloalkyl group means a C1-3alkyl group in which at least hydrogen atom is substituted by one fluorine atom, chlorine atom, bromine atom or iodine atom. Examples of the C1-3 haloalkyl group include a 2-chloroethyl group, a 2-bromoethyl group, a 2-iodoethyl group, and a 3-chloropropyl group.

The C1-3alkyl group substituted by one or two C6-12aryl groups means a C1-3alkyl group one or two hydrogen atoms of which are substituted by C6-12 aryl group. Examples of the C1-3alkyl group substituted by one or two aryl C6-12 groups include a benzyl group, a diphenylmethyl group, a 2-phenylethyl group, a 2-phenylpropyl group, a 1-methyl-1-phenylethyl group, a 2-nitrobenzyl group, a 3-nitrobenzyl group, a 4-nitrobenzyl group, a 2,4-dinitrobenzyl group, a 2,4,6-trinitrobenzyl group, a 2-phenylbenzyl group, a 3-phenylbenzyl group, a 4-phenylbenzyl group, a 2-hydroxybenzyl group, a 3-hydroxybenzyl group, a 4-hydroxybenzyl group, a 2-chlorobenzyl group, a 3-chlorobenzyl group, a 4-chlorobenzyl group, a 2-fluorobenzyl group, a 3-fluorobenzyl group, a 4-fluorobenzyl group, a 2-bromobenzyl group, a 3-bromobenzyl group, a 4-bromobenzyl group, a 2-iodobenzyl group, a 2,3-dichlorobenzyl group, a 2,4-dichlorobenzyl group, a 2,5-dichlorobenzyl group, a 2,6-dichlorobenzyl group, a 3,4-dichlorobenzyl group, a 3,5-dichlorobenzyl group, a 2-methylbenzyl group, a 3-methylbenzyl group, a 4-methylbenzyl group, a 2-ethylbenzyl group, a 3-ethylbenzyl group, a 4-ethylbenzyl group, a 2-isopropylbenzyl group, a 3-isopropylbenzyl group, a 4-isopropylbenzyl group, a 2-methoxybenzyl group, a 3-methoxybenzyl group, a 4-methoxybenzyl group, a 2,3-dimethoxybenzyl group, a 2,4-dimethoxybenzyl group, a 2,5-dimethoxybenzyl group, a 2,6-dimethoxybenzyl group, a 3,4-dimethoxybenzyl group, a 3,5-dimethoxybenzyl group, a 2-ethoxybenzyl group, a 3-ethoxybenzyl group, a 4-ethoxybenzyl group, a 2-isopropoxybenzyl group, a 3-isopropoxybenzyl group, a 4-isopropoxybenzyl group, a 2-methoxymethylbenzyl group, a 3-methoxymethylbenzyl group, a 4-methoxymethylbenzyl group, a 2-isopropoxymethylbenzyl group, a 3-isopropoxymethylbenzyl group, a 4-isopropoxymethylbenzyl group, a 2-trifluoromethyl group, a 3-trifluoromethyl group, a 4-trifluoromethyl group, a 2-hydroxycarbonylbenzyl group, a 3-hydroxycarbonylbenzyl group, a 4-hydroxycarbonylbenzyl group, a 2-aminobenzyl group, a 3-aminobenzyl group, a 4-aminobenzyl group, a 2-aminomethylbenzyl group, a 3-aminomethylbenzyl group, a 4-aminomethylbenzyl group, a 2-cyanobenzyl group, a 3-cyanobenzyl group, a 4-cyanobenzyl group, a 2-hydroxymethylbenzyl group, a 3-hydroxymethylbenzyl group, a 4-hydroxymethylbenzyl group, a 2-phenoxybenzyl group, a 3-phenoxybenzyl group and a 4-phenoxybenzyl group.

The C6-12aryl group means a polycyclic aromatic group having six to twelve carbon atoms. The examples of the C6-12aryl group include a phenyl group, a 1-naphthyl group and a 2-naphthyl group. The C6-12aryl group optionally having a substituent means a C6-12 aryl group one or two hydrogen atoms of which is substituted by other atoms or groups. Examples of the C6-12aryl group optionally having a substituent include a halogen atom, C1-3alkyl group, C1-3alkoxy group and a hydroxyC2-3 alkyl group.

Examples of the halogen atoms include a fluorine atom, a chlorine atom, a bromine atom, and an iodine atom. In the halogen atom, a fluorine atom or a chlorine atom is preferred.

A preferred embodiment of the first aspect is the ribonucleoside, the ribonucleotide, or the derivative thereof having the protective group at the 2'-position described above, wherein the substituent is represented by the following groups. In other words, $R^1$ to $R^4$ may be identical or different, and each represents a hydrogen atom, a methyl group or an ethyl group. $R^5$ and $R^6$ may be identical or different, and each represents a hydrogen atom, a halogen atom, or a $C_{1-3}$ haloalkyl group. $R^7$ represents a halogen atom.

A preferred embodiment of the first aspect is the ribonucleoside, the ribonucleotide, or the derivative thereof having a protective group at the 2'-position described above, wherein the substituent is represented by the following groups. In other words, all of $R^1$ to $R^4$ represent a hydrogen atom. $R^5$ and $R^6$ may be identical or different, and each represents a hydrogen atom, a fluorine atom, a chlorine atom or a bromine atom. $R^7$ represents a fluorine atom, a chlorine atom or a bromine atom.

A preferred embodiment of the first aspect is the ribonucleoside, the ribonucleotide, or the derivative thereof having a protective group at the 2'-position described above, wherein the substituent is represented by the following groups. In other words, all of $R^1$ to $R^5$ represent a hydrogen atom. $R^6$ represents a hydrogen atom, a fluorine atom or a chlorine atom. $R^7$ represents a fluorine atom or a chlorine atom.

A preferred embodiment of the first aspect is the ribonucleoside, the ribonucleotide, or the derivative thereof having a protective group at the 2'-position described above, wherein the substituent is represented by the following groups. In other words, all of $R^1$ to $R^5$ represent a hydrogen atom. $R^6$ represents a hydrogen atom, or a chlorine atom, and $R^7$ represents a chlorine atom.

As shown in Examples described below, a nucleic acid having a 2-chloroethoxymethyl group and a 2,2-dichloroethoxymethyl group at the 2'-position as a protective group is a novel substance having a high double strand-forming ability.

A preferred embodiment of the first aspect is the ribonucleoside, the ribonucleotide, or the derivative thereof having a protective group at the 2'-position described above, wherein when $R^7$ is a $C_{1-3}$ haloalkyl group in Formula (I), preferred examples of the $C_{1-3}$ haloalkyl group include a chloromethyl group; a dichloromethyl group; a trichloromethyl group; a 1-chloroethyl group; a 2-chloroethyl group; a 1,1-dichloroethyl group; a 1,2-dichloroethyl group; a 2,2-dichloroethyl group; a 1-chloropropyl group; a 2-chloropropyl group; a 1,1-dichloropropyl group; a 1,2-dichloropropyl group; or a 2,2-dichloropropyl group. When $R^7$ is a $C_{1-3}$ haloalkyl group, $R^1$ to $R^6$ are preferably a hydrogen atom.

A preferred embodiment of the first aspect is the following compounds when the nucleic acid base B is adenosine, guanosine, cytidine or uridine. The nucleic acid base B is a nucleic acid base constituting the ribonucleoside, the ribonucleotide, or the derivative thereof.

Namely,
2'-O-(2-chloro)ethoxymethyl-3',5'-O-(1,1,3,3-tetraisopropyldisiloxane-1,3-diyl)nucleic acid base (B),
2'-O-(2,2-dichloro)ethoxymethyl-3',5'-O-(1,1,3,3-tetraisopropyldisiloxane-1,3-diyl)nucleic acid base (B),
2'-O-(2,2,2-trichloro)ethoxymethyl-3',5'-O-(1,1,3,3-tetraisopropyldisiloxane-1,3-diyl)nucleic acid base (B),
2'-O-(2,2-difluoro)ethoxymethyl-3',5'-O-(1,1,3,3-tetraisopropyldisiloxane-1,3-diyl)nucleic acid base (B),
2'-O-(2,2,2-trifluoro)ethoxymethyl-3',5'-O-(1,1,3,3-tetraisopropyldisiloxane-1,3-diyl)nucleic acid base (B),
2'-O-(2-chloro)ethoxymethyl-5'-O-(4,4'-dimethoxytrityl)) nucleic acid base (B),
2'-O-(2,2-dichloro)ethoxymethyl-5'-O-(4,4'-dimethoxytrityl)nucleic acid base (B),
2'-O-(2,2,2-trichloro)ethoxymethyl-5'-O-(4,4'-dimethoxytrityl)nucleic acid base (B),
2'-O-(2,2-difluoro)ethoxymethyl-5'-O-(4,4'-dimethoxytrityl)nucleic acid base (B),
2'-O-(2,2,2-trifluoro)ethoxymethyl-5'-O-(4,4'-dimethoxytrityl)nucleic acid base (B),
2'-O-(2-chloro)ethoxymethyl-5'-O-(4,4'-dimethoxytrityl) nucleic acid base (B) 3'-(2-cyanoethyl diisopropylphosphoramidite),
2'-O-(2,2-dichloro)ethoxymethyl-5'-O-(4,4'-dimethoxytrityl)nucleic acid base (B) 3'-(2-cyano ethyl diisopropylphosphoramidite),
2'-O-(2,2,2-trichloro)ethoxymethyl-5'-O-(4,4'-dimethoxytrityl)nucleic acid base (B) 3'-(2-cyano ethyl diisopropylphosphoramidite),
2'-O-(2,2-difluoro)ethoxymethyl-5'-O-(4,4'-dimethoxytrityl)nucleic acid base (B) 3'-(2-cyano ethyl diisopropylphosphoramidite),
2'-O-(2,2,2-trifluoro)ethoxymethyl-5'-O-(4,4'-dimethoxytrityl)nucleic acid base (B) 3'-(2-cyano ethyl diisopropylphosphoramidite),
2'-O-(2-bromo)ethoxymethyl-3',5'-O-(1,1,3,3-tetraisopropyldisiloxane-1,3-diyl)nucleic acid base (B),
2'-O-(2,2-dibromo)ethoxymethyl-3',5'-O-(1,1,3,3-tetraisopropyldisiloxane-1,3-diyl)nucleic acid base (B),
2'-O-(2,2,2-tribromo)ethoxymethyl-3',5'-O-(1,1,3,3-tetraisopropyldisiloxane-1,3-diyl)nucleic acid base (B),
2'-O-(2-bromo)ethoxymethyl-5'-O-(4,4'-dimethoxytrityl) nucleic acid base (B) 3'-(2-cyanoethyl diisopropylphosphoramidite),
2'-O-(2,2-dibromo)ethoxymethyl-5'-dimethoxytrityl)nucleic acid base (B) 3'-(2-cyano ethyl diisopropylphosphoramidite),
or 2'-O-(2,2,2-tribromo)ethoxymethyl-5'-O-(4,4'-dimethoxytrityl)nucleic acid base (B) 3'-(2-cyano ethyl diisopropylphosphoramidite) is preferred.

A bromine-substituted body including a 2-bromoethoxymethyl group is regarded as a useful compound similarly to a chlorine-substituted body.

A preferred embodiment of the first aspect is
2'-O-(2-chloro)ethoxymethyl-5'-O-(4,4'-dimethoxytrityl) nucleic acid base B 3'-(2-cyanoethyldiisopropyl phosphoramidite), or
2'-O-(2,2-dichloro)ethoxymethyl-5'-O-(4,4'-dimethoxytrityl)nucleic acid base B 3'-(2-cyanoethyldiisopropyl phosphoramidite) when the nucleic acid base B is adenosine, guanosine, cytidine or uridine.

A second aspect of the invention relates to a method of manufacturing a ribonucleoside, a ribonucleotide, or a derivative thereof represented by the following Formula (I) and having a protective group at the 2'-position. As the ribonucleoside, the ribonucleotide, or the derivative thereof in this method, any one of the compounds described in the first aspect can be adopted. This method includes a process of reacting a compound represented by the following Formula (III) with a compound represented by the following Formula (II).

[Chemical Formula 2]

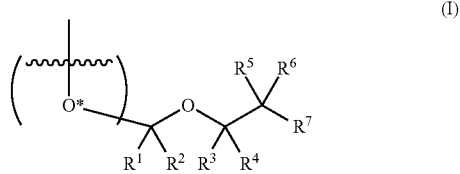

(I)

(In Formula (I), O* represents an oxygen atom of a hydroxyl group at the 2' position of the ribonucleoside, the ribonucleotide, or the derivative thereof, and
$R^1$ to $R^7$ are the same as described above.)

[Chemical Formula 3]

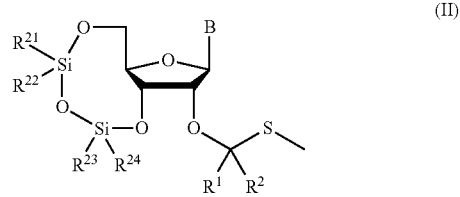

(II)

(In Formula (II), B represents a nucleic acid base that may be protected with a protective group, $R^{21}$, $R^{22}$, $R^{23}$ and $R^{24}$ may be identical or different, and each represents a $C_{1-5}$ alkyl group, a $C_{1-5}$ alkoxy group or a $C_{1-5}$ haloalkyl group that may be straight or branched, and $R^1$ and $R^2$ represent the same as $R^1$ and $R^2$ in Formula (I).)

The nucleic acid base in the "nucleic acid base that may be protected with a protective group" means a substituent including the base contained in RNA, and specific examples thereof include adenosine, guanosine, cytidine or uridine. Examples of the nucleic acid base in the invention include adenine, guanine, cytosine, uracil or a derivative thereof. Examples of the derivative of the nucleic acid base include 5-methyl cytosine; 5-hydroxymethyl cytosine; 5-fluorouracil; thiouracil; 6-azauracil; 5-hydroxyuracil; 2,6-diaminopurine; azadenine; azaguanine; and isoguanine.

Examples of the nucleic acid base protected with a protective group in the "nucleic acid base that may be protected with a protective group" include nucleic acid bases in which an atom in an amino group in the nucleic acid base is substituted with a group that can be eliminated. Examples of the protective group of the amino group in the nucleic acid base include aliphatic acyl groups such as an acetyl group, a propionyl group, a butyryl group, and an isobutyryl group; aromatic acyl groups such as a benzoyl group, a 4-methyl benzoyl group, a 4-methoxybenzoyl group, a phenylacetyl group, a phenoxyacetyl group, a 4-tert-butylphenoxyacetyl group; and a 4-isopropylphenoxyacetyl group; an aliphatic acyl group or aromatic acyl group having substituents such as a halogen atom, a $C_{1-10}$ alkyl group, and a $C_{1-10}$ alkyloxy group; a 2-cyanoethyl group; a 2-(p-nitrophenyl)ethyl group; a 2-(benzene sulfonyl)ethyl group; a dimethylaminomethylene group; a dibutylaminomethylene group; a 2-cyanoethoxycarbonyl group; a 2-(p-nitrophenyl) ethoxycarbonyl group; and a 2-(benzene sulfonyl)ethoxycarbonyl group.

The C1-5alkyl group means an alkyl group having one to five carbon atoms. Examples of the straight-chain C1-5alkyl group include a methyl group, an ethyl group, a propyl group, butyl group and a pentyl group. Examples of the branched chain C1-5alkyl group include an isopropyl group, an isobutyl group, a 1-methylpropyl group, a t-butyl group, a 1-methylbutyl group, a 2-methylbutyl group, a 3-methylbutyl group, a 1-ethylpropyl group, a 1,1-dimethylpropyl group, a 2,2-dimethylpropyl group, a 1,2-dimethylpropyl group. Examples of the cyclic C1-3alkyl group include a cyclopropyl group, a cyclobutyl group, and a cyclopentyl group.

The C1-5alkoxy group means an alkoxy group having one to five carbon atoms. Examples of the C1-5alkoxy group include a methoxy group, an ethoxy group and a propyloxy group.

The C1-5haloalkyl group means a haloalkyl group having one to five carbon atoms.

Preferred examples of $R^{21}$ to $R^{24}$ include a $C_{2-4}$ alkyl group, and specific examples of $R^{21}$ to $R^{24}$ include an ethyl group, a propyl group, an isopropyl group, an n-butyl group, a sec-butyl group, an isobutyl group, or a ter-butyl group.

[Chemical Formula 4]

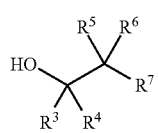

(III)

(In Formula (III), $R^3$ to $R^7$ represent the same as $R^3$ to $R^7$ in Formula (I).)

In this process, for example, the compound represented by Formula (II) is dried by an appropriate solvent, and then dissolved in a solvent. Examples of the solvent include THF. To this solution, the compound represented by Formula (III) is added. The solution is cooled to equal to or higher than $-50°$ C. and equal to or lower than $-20°$ C., preferably equal to or higher than $-45°$ C. and equal to or lower than $-30°$ C. Then, a halogen source such as NIS and NBS, and an organic acid such as toluenesulfonic acid and trifluoromethanesulfonic acid are added while stirring. Examples of the stirring time include equal to or longer than 30 minutes and equal to or shorter than 2 hours. A base such as triethyl amine may be added in order to stop the reaction. Then, the reaction solution is purified. By such procedures, a ribonucleoside represented by the following Formula (IV) can be obtained. With use of the compound represented by Formula (IV), a compound represented by Formula (I) as described below can be obtained.

The second aspect of the invention preferably includes the following process after the above-described process. In other words, in the process described above, the compound represented by Formula (III) is reacted with the compound represented by Formula (II) to obtain a compound represented by the following Formula (IV). Then, the compound represented by Formula (IV) is reacted with a $C_{1-3}$ alcohol for de-protection, whereby to obtain a compound represented by the following Formula (V).

[Chemical Formula 5]

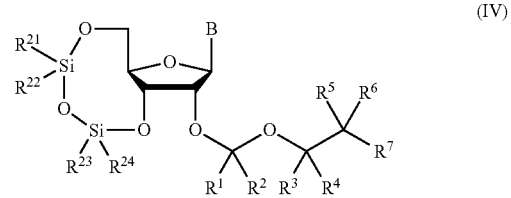

(IV)

In Formula (IV), B represents a nucleic acid base that may be protected with a protective group, $R^1$ to $R^7$ represent the same as $R^1$ to $R^7$ in Formula (I), and $R^{21}$ to $R^{24}$ represent the same as $R^{21}$ to $R^{24}$ in Formula (II). The nucleic acid base that may be protected with a protective group represents the same as those in Formula (II).

[Chemical Formula 6]

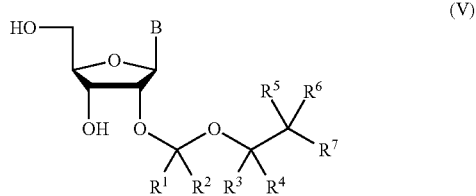

(V)

In Formula (V), B represents a nucleic acid base that may be protected with a protective group, and $R^1$ to $R^7$ represent the same as $R^1$ to $R^7$ in Formula (I).

This process is performed, for example, after drying the compound represented by Formula (IV). Then, the compound represented by Formula (IV) is dissolved in a $C_{1-3}$ alcohol (lower alcohol). Examples of the lower alcohol include methanol or ethanol. To the solution, for example, ammonium fluoride is added, and the reaction mixture is stirred. The temperature at the time of the stirring may be equal to or higher than 30° C. and equal to or lower than 60° C., or equal to or higher than 45° C. and equal to or lower than 55° C. The reaction time may be equal to or longer than for 3 hours and equal to or shorter than 1 day, or equal to or longer than for 4 hours and equal to or shorter than for 7 hours. The obtained compound is concentrated or extracted with a known method.

Next, the compound represented by Formula (V) is reacted with dimethoxytriphenylmethyl halide, to obtain a compound represented by Formula (VI).

[Chemical Formula 7]

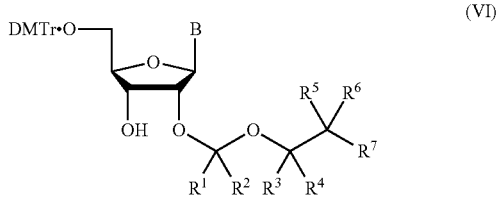

(VI)

In Formula (VI), B represents a nucleic acid base that may be protected with a protective group, $R^1$ to $R^7$ represent the same as $R^1$ to $R^7$ in Formula (I), and the formula DMTr represents a 4,4'-dimethoxytrityl group.

Examples of the dimethoxytriphenylmethyl halide include 4,4'-dimethoxytrityl chloride.

The second aspect of the invention preferably further includes the following process after the process described above. In other words, the second aspect of the invention includes a process of reacting the compound represented by Formula (VI), which has been obtained in the process described above, with a compound represented by the following Formula (VII), to obtain a compound represented by the following Formula (VIII).

[Chemical Formula 8]

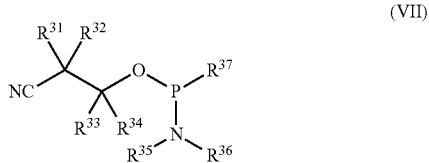

(VII)

(In Formula (VII), $R^{31}$ to $R^{34}$ may be identical or different, and each represents a hydrogen atom, a $C_{1-3}$ alkyl group, or a $C_{1-3}$ haloalkyl group, $R^{35}$ and $R^{36}$ may be identical or different, and each represents a $C_{1-5}$ alkyl group or a $C_{1-5}$ haloalkyl group, and $R^{37}$ represents a halogen atom.)

Preferred examples of $R^{31}$ to $R^{34}$ may be identical or different, and each represents a hydrogen atom, or a methyl group. Meanwhile, all of $R^{31}$ to $R^{34}$ are most preferably a hydrogen atom.

Preferred examples of $R^{35}$ and $R^{36}$ include a $C_{2-4}$ alkyl group, and specific examples of $R^{21}$ to $R^{24}$ include an ethyl group, a propyl group, an isopropyl group, an n-butyl group, a sec-butyl group, an isobutyl group, or a ter-butyl group.

Preferred examples of $R^{37}$ include a fluorine atom, a chlorine atom or a bromine atom.

[Chemical Formula 9]

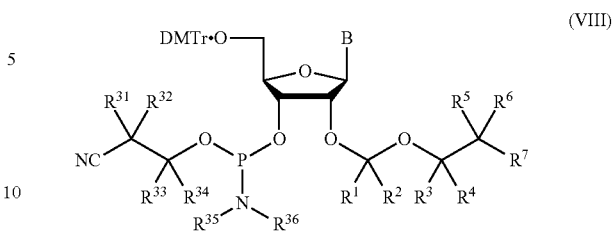

(VIII)

(In Formula (VIII), B represents a nucleic acid base that may be protected with a protective group, $R^1$ to $R^7$ represent the same as $R^1$ to $R^7$ in Formula (I), $R^{31}$ to $R^{36}$ represent the same as $R^{31}$ to $R^{36}$ in Formula (VII), and the formula DMTr represents a 4,4'-dimethoxytrityl group.)

In this process, the compound represented by Formula (VI) is suitably dried. This compound is dissolved in a solvent, and the compound represented by formula (VII) is dropped thereto. The reaction solution is stirred, for example, at a temperature of equal to or higher than 20° C. and equal to or lower than 30° C. for equal to or longer than 30 minutes and equal to or shorter than 2 hours. A lower alcohol may be added in order to stop the reaction.

Advantageous Effects of Invention

The invention can impart a high double strand-forming ability basically by introducing a halogen atom as a substituent into the moiety of the protective group of the modified body of RNA having an alkoxymethyl-based protective group.

In addition, the invention can easily synthesize the modified body of RNA regardless of the kind of the nucleic acid base of RNA by introducing a halogen atom as a substituent into the moiety of the protective group of the modified body of RNA having an alkoxymethyl skeleton.

DESCRIPTION OF EMBODIMENT

Figure 1:
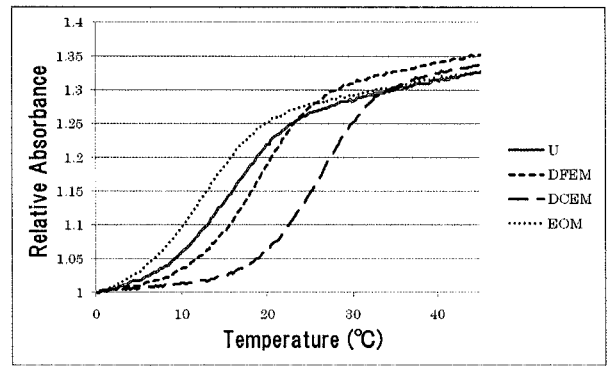
FIG. 1 is a graph, instead of a drawing, illustrating the influence of a substituent with respect to an alkoxymethyl skeleton modification.

As described above, the first aspect of the invention relates to a ribonucleoside, a ribonucleotide, or a derivative thereof having a protective group at the 2'-position. The protective group is represented by the following Formula (I) when an oxygen atom at the 2'-position of the ribonucleoside, the ribonucleotide, or the derivative thereof is expressed as O*.

[Chemical Formula 10]

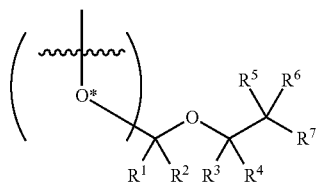

(I)

In the formula, O* represents the oxygen atom of the hydroxyl group at the 2' position of the ribonucleoside, the ribonucleotide, or the derivative thereof. Meanwhile, the site connected to O* is the moiety of the protective group. For this reason, the moiety including the ribose and the nucleic acid base in Formula (I) is enclosed in the parentheses. The ribonucleotide is a unit constituting RNA. The ribonucleoside includes a ribose and a nucleic acid base. A ribonucleoside phosphate is a ribonucleotide. A derivative of the ribonucleoside or the ribonucleotide is those obtained by adding one or multiple substituents to a ribonucleoside or ribonucleotide constituting RNA. Examples of the substituent include a $C_{1-3}$ alkyl group, or a $C_{1-3}$ haloalkyl group that substitutes a hydrogen atom of the ribonucleoside or ribonucleotide.

In Formula (I), $R^1$ and $R^2$ may be identical or different, and each represents a hydrogen atom, a $C_{1-3}$ alkyl group, a $C_{2-3}$ alkenyl group, a $C_{2-3}$ alkynyl group, a hydroxy $C_{2-3}$ alkyl group, or a $C_{1-3}$ haloalkyl group. $R^3$ and $R^4$ may be identical or different, and each represents a hydrogen atom, a halogen atom, a $C_{1-3}$ alkyl group, a $C_{2-3}$ alkenyl group, a $C_{2-3}$ alkynyl group, a hydroxy $C_{2-3}$ alkyl group, or a $C_{1-3}$ haloalkyl group. $R^5$ and $R^6$ may be identical or different, and each represents a hydrogen atom, a halogen atom, a $C_{1-3}$ alkyl group, a $C_{2-3}$ alkenyl group, a $C_{2-3}$ alkynyl group, a hydroxy $C_{2-3}$ alkyl group or a $C_{1-3}$ haloalkyl group. $R^7$ represents a halogen atom or a $C_{1-3}$ haloalkyl group.

The invention also provides oligo ribonucleic acid (oligo RNA) containing the ribonucleoside, the ribonucleotide, or the derivative thereof. The oligo ribonucleic acid (oligo RNA) becomes a material for a pharmaceutical product containing antisense RNA, siRNA, and an aptamer. For this reason, the invention also provides a reagent, a reagent for antisense RNA, a reagent for siRNA, and a reagent for an aptamer containing the ribonucleoside, the ribonucleotide, or the derivative thereof.

As explained previously, the second aspect of the invention relates to a method of manufacturing a ribonucleoside, a ribonucleotide, or a derivative thereof having a protective group at the 2'-position. With respect to this manufacturing method, those adjusted by suitably adopting a known method by one of ordinary skill in the art based on the Examples described below are also encompassed in the second aspect of the invention.

Hereinafter, Examples will be represented, and the invention will be specifically explained. However, the invention is not limited to the Examples, and those suitably modified within an obvious range by one of ordinary skill in the art are also encompassed in the invention.

Example 1

Measurement System

In measurement of NMR [$^1$H NMR (300 MHz), $^{31}$P NMR (121 MHz)], Varian MERCURY 300 (300 MHz) was used. In $^1$H NMR, tetramethylsilane (TMS) (δ0.0) in CDCl$_3$ was used as an external standard. In $^{31}$P NMR, 85% H$_3$PO$_4$ (δ0.0) was used as an external standard. In measurement of UV/vis spectrum, JASCO V-550 UV/vis spectrophotometer was used. In measurement of MALDI-TOF-MS, Applied Biosystems Voyager-DE STR spectrometer was used. In thin layer chromatography (TLC), TLC plates Silica gel 60 F$_{254}$ (Merck, No. 5715) was used. In silica gel column chromatography, Kanto silica gel 60N (spherical, neutral, 63-210 micrometer) was used. In Reversed-phase HPLC (RP-HPLC), μBondasphere 5 μm C18 column (100 Angstrom, 3.9 mm×150 mm) (Waters), or Source 5RPC ST 4.6/150 (4.6 mm×150 mm) (GE Healthcare) was used. As the solvent used in reaction, a commercial solvent was appropriately distilled, and dried with sodium or molecular sieve (MS), was used. All of the reactions were performed under argon (Ar) atmosphere.

Synthesis of 2'-O-haloalchoxymethyl-5'-O-(4,4'-dimethoxytrityl)uridine 3'-(2-cyanoethyl diisopropylphosphoramidite)

Schemes 1 to 3 below were performed with reference to the method described in Ohgi, T.; Kitagawa, H.; Yano, J.; *Current Protocols in Nucleic Acid Chemistry*, 2008, 2.15.1-2.15.19.

Preparation of 2'-O-haloalchoxymethyl-3',5'-O-(1,1,3,3-tetraisopropyldisiloxane-1,3-diyl)uridine (2a-e)

Scheme 1

[Chemical Formula 11]

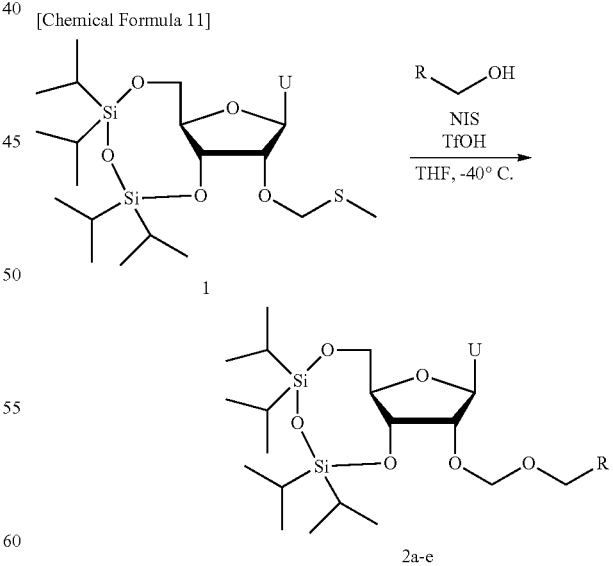

2a: R = CH$_2$Cl
2b: R = CHCl$_2$
2c: R = CCl$_3$
2d: R = CHF$_2$
2e: R = CF$_3$

In Scheme 1, NIS represents N-iodosuccinimide. TfOH represents trifluoromethane sulfonic acid. THF represents tetrahydrofuran.

2'-O-(2-chloro)ethoxymethyl-3',5'-O-(1,1,3,3-tetraisopropyldisiloxane-1,3-diyl)uridine (2a)

The compound represented by Formula 1, 2'-O-methylthiomethyl-3',5'-O-(1,1,3,3-tetraisopropyldisiloxane-1,3-diyl)uridine (1) (1.09 g, 2 mmol) was dissolved in THF (7 ml) by performing azeotropic drying by pyridine and toluene. To this mixture, 2-chloroethanol (268 ml, 4 mmol) was added, and the reaction mixture was cooled to −40° C. Then, N-iodosuccinimide (540 mg, in 5.4 ml of 2.4 mmol THF) was added, and trifluoromethane sulfonic acid (351 ml, in 7 ml of 2 mmol THF) was dropped. The reaction mixture was stirred at −40° C. for 1 hour, and then 7 ml of triethyl amine was added to stop the reaction. To this mixture, dichloromethane (60 ml) was added, and the reaction mixture was washed with 10% $Na_2S_2O_3$ aqueous solution (40 ml×2) and saturated sodium bicarbonate water (40 ml×2), and the collected washing liquid was extracted with dichloromethane (60 ml). The collected organic layers were dried with anhydrous sodium sulfate, and then filtered, and dried and concentrated under reduced pressure, and the resultant was purified with silica gel chromatography [3×10 cm, 30 g of silica gel, dichloromethane-methanol (99.5:0.5, v/v→99:1, v/v)], whereby to obtain a compound represented by Formula 2a (1.06 g, 92%).

1H NMR (300 MHz, CDCl3) d 9.51 (1H, br, NH), d 7.90 (1H, d, J=8.1 Hz, 6-H), d 5.75 (1H, s, 1'-H), d 5.69 (1H, d, J=8.4 Hz, 5-H), d 5.05 (1H, d, J=6.9 Hz, H—C of acetal), d 4.99 (1H, d, J=6.9 Hz, H—C of acetal), d 4.29-3.67 (9H, m, 2'-H, 3'-H, 4'-H, 5'-H, CH2Cl—CH2-O), d 1.11-0.93 (28H, m, iPr×4).

2'-O-(2,2-dichloro)ethoxymethyl-3',5'-O-(1,1,3,3-tetraisopropyldisiloxane-1,3-diyl)uridine (2b)

2'-O-methylthiomethyl-3',5'-O-(1,1,3,3-tetraisopropyldisiloxane-1,3diyl)uridine (820 mg, 1.5 mmol) represented by Formula 1 was dissolved in THF (10 ml) by performing azeotropic drying by pyridine and toluene. To this mixture, 2,2-dichloroethanol (250 ml, 3 mmol) and molecular sieves 4A (1.6 g) were added, and the reaction mixture was cooled to −40° C., and then N-iodosuccinimide (420 mg, 1.8 mmol) was added, and trifluoromethane sulfonic acid (270 ml, 3 mmol) was dropped. The reaction mixture was stirred at −40° C. for 1 hour, and then 5 ml of triethyl amine was added to stop the reaction. To this mixture, dichloromethane (40 ml) was added, and the reaction mixture was washed with 10% $Na_2S_2O_3$ aqueous solution (30 ml×2) and saturated sodium bicarbonate water (30 ml×2), and the collected washing liquid was extracted with dichloromethane (40 ml). The collected organic layer was dried with anhydrous sodium sulfate, and then filtered, and dried and concentrated under reduced pressure, and the resultant was purified with silica gel chromatography [2×10 cm, 20 g of silica gel, dichloromethane-methanol (99.5:0.5, v/v→97:3, v/v)], whereby to obtain the compound represented by Formula 2b (761 mg, 83%).

1H NMR (300 MHz, CDCl3) d 8.09 (1H, br, NH), d 7.89 (1H, d, J=8.4 Hz, 6-H), d 5.86 (1H, t, CHCl2-CH2-O), d 5.72 (1H, s, 1'-H), d 5.69-5.66 (1H, m, 5-H), d 5.09 (1H, d, J=6.6 Hz, H—C of acetal), d 5.02 (1H, d, J=6.9 Hz, H—C of acetal), d 4.29-3.96 (7H, m, 2'-H, 3'-H, 4'-H, 5'-H, CHCl2-CH2-O), d 1.11-0.93 (28H, m, iPr×4).

2'-O-(2,2,2-trichloro)ethoxymethyl-3',5'-O-(1,1,3,3-tetraisopropyldisiloxane-1,3-diyl)uridine (2c)

2'-O-methylthiomethyl-3',5'-O-(1,1,3,3-tetraisopropyldisiloxane-1,3diyl)uridine represented by Formula 1 (1.09 g, 2 mmol) was dissolved in THF (14 ml) by performing azeotropic drying by pyridine and toluene. To this mixture, 2,2,2-trichloroethanol (970 ml, 10 mmol) and molecular sieves 4A (1.5 g), and N-iodosuccinimide (545 mg, 2.4 mmol) were added, and the reaction mixture was cooled to −40° C., and then trifluoromethane sulfonic acid (351 ml, 4 mmol) was dropped. The reaction mixture was stirred at −40° C. for 1 hour, and then 1.5 ml of triethyl amine was added to stop the reaction. To this mixture, dichloromethane (60 ml) was added, and the reaction mixture was washed with 10% $Na_2S_2O_3$ aqueous solution (40 ml×2) and saturated sodium bicarbonate water (40 ml×2), and the collected washing liquid was extracted with dichloromethane (40 ml×2). The collected organic layer was dried with anhydrous sodium sulfate, and then filtered, and dried and concentrated under reduced pressure, and the resultant was purified with silica gel chromatography [3×17 cm, 25 g of silica gel, dichloromethane-methanol (99.5:0.5, v/v→99:1, v/v)], whereby to obtain a compound represented by Formula 2c (826 mg, 64%).

1H NMR (300 MHz, CDCl3) d 8.35 (1H, br, NH), d 7.89 (1H, d, J=7.5 Hz, 6-H), d 5.75 (1H, s, 1'-H), d 5.68 (1H, d, J=7.8 Hz, 5-H), d 5.23 (1H, d, J=6.6 Hz, H—C of acetal), d 5.16 (1H, d, J=6.9 Hz, H—C of acetal), d 4.35-3.96 (7H, m, 2'-H, 3'-H, 4'-H, 5'-H, CCl3-CH2-O), d 1.11-0.96 (28H, m, iPr×4).

2-O-(2,2-difluoro)ethoxymethyl-3',5'-O-(1,1,3,3-tetraisopropyldisiloxane-1,3-diyl)uridine (2d)

2'-O-methylthiomethyl-3',5'-O-(1,1,3,3-tetraisopropyldisiloxane-1,3diyl)uridine represented by Formula 1 (3.25 g, 6 mmol) was dissolved in THF (38 ml) by performing azeotropic drying by pyridine and toluene. To this mixture, 2,2-difluoroethanol (760 ml, 12 mmol), and molecular sieves 4A were added, and the reaction mixture was cooled to −40° C., and then N-iodosuccinimide (1.62 g, 7.2 mmol) was added, and trifluoromethane sulfonic acid (760 ml, 12 mmol) was dropped. The reaction mixture was stirred at −40° C. for 1 hour, and then 10 ml of triethyl amine was added to stop the reaction. To this mixture, dichloromethane (150 ml) was added, and the reaction mixture was washed with 10% $Na_2S_2O_3$ aqueous solution (150 ml×2) and saturated sodium bicarbonate water (150 ml×2), and the collected washing liquid was extracted with dichloromethane (50 ml×2). The collected organic layer was dried with anhydrous sodium sulfate, and then filtered, and dried and concentrated under reduced pressure, and the resultant was purified with silica gel chromatography [4×16 cm, 80 g of silica gel, dichloromethane-methanol (99.5:0.5, v/v→99:1, v/v)], whereby to obtain a compound represented by Formula 2d (2.85 g, 83%).

1H NMR (300 MHz, CDCl3) d 8.90 (1H, br, NH), d 7.90 (1H, d, J=8.1 Hz, 6-H), d 6.17-5.77 (1H, m, CHF2-CH2-O), d 5.73 (1H, s, 1'-H), d 5.69 (1H, d, J=7.5 Hz, 5-H), d 5.06 (1H, d, J=6.9 Hz, H—C of acetal), d 4.97 (1H, d, J=6.9 Hz, H—C of acetal), d 4.29-3.77 (7H, m, 2'-H, 3'-H, 4'-H, 5'-H, CHF2-CH2-O), d 1.14-0.91 (28H, m, iPr×4).

2'-O-(2,2,2-trifluoro)ethoxymethyl-3',5'-O-(1,1,3,3-tetraisopropyldisiloxane-1,3-diyl)uridine (2e)

2'-O-methylthiomethyl-3',5'-O-(1,1,3,3-tetraisopropyldisiloxane-1,3diyl)uridine (1.09 g, 2 mmol) represented by Formula 1 was dissolved in THF (12 ml) by performing azeotropic drying by pyridine and toluene. To this mixture, 2,2,2-trifluoroethanol (288 ml, 4 mmol) and molecular sieves 4A (1 g) were added, and the reaction mixture was cooled to −40° C., and then N-bromosuccinimide (540 mg, 2.4 mmol) was added, and p-toluene sulfonic acid (288 ml, 4 mmol) was dropped. The reaction mixture was stirred at −40° C. for 1 hour, and then 3 ml of triethyl amine was added to stop the reaction. To this mixture, dichloromethane (60 ml) was added, and the reaction mixture was washed with 10% $Na_2S_2O_3$ aqueous solution (40 ml×2) and saturated sodium bicarbonate water (40 ml×2), and the collected washing liquid was extracted with dichloromethane (40 ml×2). The collected organic layer was dried with anhydrous sodium sulfate, and then filtered, and dried and concentrated under reduced pressure, and the resultant was purified with silica gel chromatography [4×8 cm, 40 g of silica gel, dichloromethane-methanol (99.5:0.5, v/v→99:1, v/v)]. The compound represented by Formula 2e could be obtained, but by-product regarded as an anomeric isomer was difficult to remove, and thus was used as it was in the next reaction without performing further purification.

Example 2

Synthesis of 2'-O-haloalchoxymethyl-5'-O-(4,4'-dimethoxytrityl)uridine (4a-e)

Scheme 2

[Chemical Formula 12]

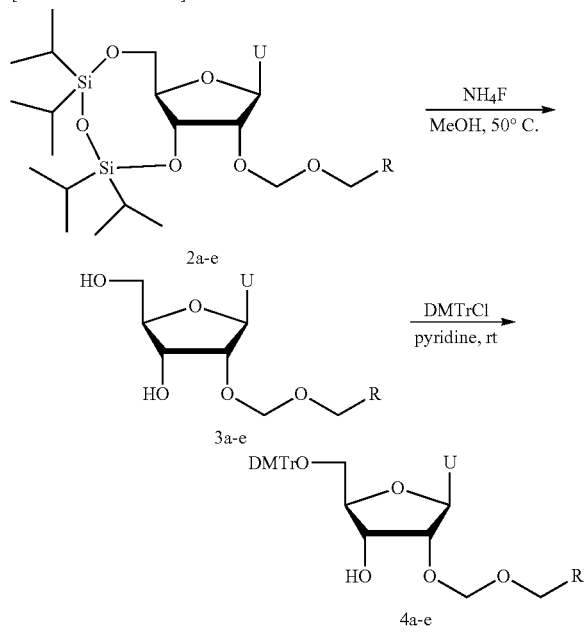

2a: R = $CH_2Cl$
2b: R = $CHCl_2$
2c: R = $CCl_3$
2d: R = $CHF_2$
2e: R = $CF_3$

In the Scheme 2, MeOH represents methanol. DMTrCl represents 4,4'-dimethoxytrityl chloride. Pyridine represents pyridine. The rt represents room temperature.

2'-O-(2-chloro)ethoxymethyl-5'-O-(4,4'-dimethoxytrityl)uridine (4a)

2'-O-2-chloroethoxymethyl-3',5'-O-(1,1,3,3-tetraisopropyldisiloxane-1,3diyl)uridine (869 mg, 1.5 mmol) represented by Formula 2a was dissolved in methanol (7.5 ml) by performing azeotropic drying by pyridine. To this mixture, ammonium fluoride (222 mg, 6 mmol) was added, and the reaction mixture was stirred at 50° C. for 7 hours. The reaction mixture was concentrated under reduced pressure, acetonitrile (30 ml) was added, and the insoluble matters were removed by filtration. This was washed with hexane (30 ml×2), and the collected washing liquid was extracted with acetonitrile (30 ml). The collected organic layer was concentrated under reduced pressure, and used in the next reaction without performing further purification. The crude purified matter was dissolved in pyridine (15 ml) by performing azeotropic drying by pyridine. To this mixture, 4,4'-dimethoxytrityl chloride (DMTrCl) (730 mg, 2.25 mmol) was added, and the reaction mixture was stirred at room temperature for 3 days. The reaction was stopped with methanol (1.5 ml), and then the solvent was distilled away under reduced pressure, and dichloromethane (40 ml) was added. This was washed with saturated sodium bicarbonate water (40 ml×3), and the collected washing liquid was extracted with dichloromethane (40 ml×2). The collected organic layer was dried with anhydrous sodium sulfate, and then filtered, and dried and concentrated under reduced pressure, and the resultant was purified with silica gel chromatography [3×14 cm, 40 g of silica gel, dichloromethane-methanol-pyridine (99.5:0:0.5, v/v/v→96.5:3:0.5, v/v/v)], whereby to obtain a compound represented by Formula 4a (754 mg, 79%).

1H NMR (300 MHz, CDCl3) d 9.35 (1H, br, NH), d 7.94 (1H, d, J=8.1 Hz, 6-H), d 7.40-6.82 (13H, m, DMTr), d 6.03 (1H, d, J=2.7 Hz, 1'-H), d 5.33-5.30 (1H, m, 5-H), d 5.03 (1H, d, J=6.9 Hz, H—C of acetal), d 4.93 (1H, d, J=6.9 Hz, H—C of acetal), d 4.50 (1H, m, 3'-H), d 4.36-4.33 (1H, m, 2'-H), d 4.09-4.07 (1H, m, 4'-H), d 3.89-3.63 (8H, m, MeO×2, CH2Cl—CH2-O), d 3.54-3.52 (2H, m, 5'-H), d 2.74 (1H, d, 3'-OH).

2'-O-(2,2-dichloro)ethoxymethyl-5'-O-(4,4'-dimethoxytrityl)uridine (4b)

2'-O-(2,2-dichloro)ethoxymethyl-3',5'-O-(1,1,3,3-tetraisopropyldisiloxane-1,3diyl)uridine, the compound represented by Formula 2b (531 mg, 865 mmol) was dissolved in methanol (5 ml) by performing azeotropic drying by pyridine and toluene. To this mixture, ammonium fluoride (132 mg, 3.56 mmol) was added, and the reaction mixture was stirred at 50° C. for 4 hours. The reaction mixture was concentrated under reduced pressure, and acetonitrile (30 ml) was added, and the insoluble matters were removed by filtration. This was washed with hexane (30 ml×2), and the collected washing liquid was extracted with acetonitrile (20 ml). The collected organic layer was concentrated under reduced pressure, and used in the next reaction without performing further purification. The crude purified matter was dissolved in pyridine (10 ml) by performing azeotropic drying by pyridine. To this mixture, DMTrCl (290 mg, 850 mmol) was added, and the reaction mixture was stirred at room temperature for 10 hours. The reaction was stopped with methanol (2 ml), and then the solvent was distilled away under reduced pressure, and dichloromethane (15 ml) was added. This was washed with saturated sodium bicarbonate water (10 ml×3), and the collected washing liquid was extracted with dichloromethane (10 ml×2). The collected organic layer was dried with anhydrous sodium sulfate, and then filtered, and dried and concentrated under reduced pressure, and the resultant was purified with silica gel chromatography [3×14 cm, 40 g of silica gel, dichloromethane-methanol-pyridine (99.5:0:0.5, v/v/v→98.5:1:0.5, v/v/v)], whereby to obtain a compound represented by Formula 4b (470 mg, 86%).

1H NMR (300 MHz, CDCl3) d 8.24 (1H, br, NH), d 7.96 (1H, d, J=8.1 Hz, 6-H), d 7.39-6.83 (13H, m, DMTr), d 6.01 (1H, d, J=2.7 Hz, 1'-H), d 5.80 (1H, t, CHCl2-CH2-O), d 5.78-5.31 (1H, m, 5-H), d 5.11 (1H, d, J=6.9 Hz, H—C of acetal), d 4.98 (1H, d, J=6.6 Hz, H—C of acetal), d 4.53-4.46 (1H, m, 3'-H), d 4.35-4.32 (1H, m, 2'-H), d 4.06-4.04 (1H, m, 4'-H), d 4.02-4.00 (2H, m, CHCl2-CH2-O), d 3.80 (6H, s, MeO×2), d 3.61-3.51 (2H, m, 5'-H), d 2.41 (1H, d, 3'-OH).

2'-O-(2,2,2-trichloro)ethoxymethyl-5'-O-(4,4'-dimethoxytrityl)uridine (4c)

2'-O-(2,2,2-trichloro)ethoxymethyl-3',5'-O-(1,1,3,3-tetraisopropyldisiloxane-1,3diyl)uridine, the compound represented by Formula 2c (650 mg, 1 mmol) was dissolved in methanol (5 ml) by performing azeotropic drying by pyridine and toluene. To this mixture, ammonium fluoride (148 mg, 4 mmol) was added, and the reaction mixture was stirred at 50° C. for 7 hours. The reaction mixture was concentrated under reduced pressure, and acetonitrile (20 ml) was added, and the insoluble matters were removed by filtration. This was washed with hexane (20 ml×2), and the collected washing liquid was extracted with acetonitrile (20 ml). The collected organic layer was concentrated under reduced pressure, and used in the next reaction without performing further purification. The crude purified matter was dissolved in pyridine (10 ml) by performing azeotropic drying by pyridine. To this mixture, DMTrCl (510 mg, 1.51 mmol) was added, and the reaction mixture was stirred at room temperature for 18 hours. The reaction was stopped with methanol (1 ml), and then the solvent was distilled away under reduced pressure, and dichloromethane (30 ml) was added. This was washed with saturated saline (30 ml×3), and the collected washing liquid was extracted with dichloromethane (30 ml). The collected organic layer was dried with anhydrous sodium sulfate, and then filtered, and dried and concentrated under reduced pressure, and the resultant was purified with silica gel chromatography [2×10 cm, 25 g of silica gel, dichloromethane-methanol-pyridine (99.5:0:0.5, v/v/v→98.5:1:0.5, v/v/v)], whereby to obtain a compound represented by Formula 4c (621 mg, 88%).

1H NMR (300 MHz, CDCl3) d 8.27 (1H, br, NH), d 7.95 (1H, d, J=7.8 Hz, 6-H), d 7.40-6.83 (13H, m, DMTr), d 6.04 (1H, d, J=3.0 Hz, 1'-H), d 5.33-5.29 (1H, m, 5-H), d 5.22 (1H, d, J=6.9 Hz, H—C of acetal), d 5.11 (1H, d, J=6.9 Hz, H—C of acetal), d 4.52-4.48 (1H, m, 3'-H), d 4.41-4.39 (1H, m, 2'-H), d 4.29-4.20 (2H, m, CCl3-CH2-O), d 4.10-4.08 (1H, m, 4'-H), d 3.80 (6H, s, MeO×2), d 3.57-3.53 (2H, m, 5'-H), d 2.42 (1H, d, 3'-OH).

2'-O-(2,2-difluoro)ethoxymethyl-5'-O-(4,4'-dimethoxytrityl)uridine (4d)

2'-O-(2,2-difluoro)ethoxymethyl-3',5'-O-(1,1,3,3-tetraisopropyldisiloxane-1,3diyl)uridine, the compound represented by Formula 2d (1.16 g, 2 mmol) was dissolved in methanol (10 ml) by performing azeotropic drying by pyridine and toluene. To this mixture, ammonium fluoride (296 mg, 8 mmol) was added, and the reaction mixture was stirred at 50° C. for 7 hours. The reaction mixture was concentrated under reduced pressure, and acetonitrile (40 ml) was added, and the insoluble matters were removed by filtration. This was washed with hexane (50 ml×2), and the collected washing liquid was extracted with acetonitrile (30 ml). The collected organic layer was concentrated under reduced pressure, and used in the next reaction without performing further purification. The crude purified matter was dissolved in pyridine (20 ml) by performing azeotropic drying by pyridine. To this mixture, DMTrCl (1.42 g, 4.2 mmol) was added, and the reaction mixture was stirred at room temperature for 3 days. The reaction was stopped with methanol (2 ml), and then the solvent was distilled away under reduced pressure, and dichloromethane (30 ml) was added. This was washed with saturated sodium bicarbonate water (30 ml×3), and the collected washing liquid was extracted with chloroform (30 ml). The collected organic layer was dried with anhydrous sodium sulfate, and then filtered, and dried and concentrated under reduced pressure, and the resultant was purified with silica gel chromatography [3×8 cm, 20 g of silica gel, dichloromethane-methanol-pyridine (99.5:0:0.5, v/v/v→96.5:3:0.5, v/v/v)], whereby to obtain a compound represented by Formula 4d (376 mg, 90%).

1H NMR (300 MHz, CDCl3) d 8.25 (1H, br, NH), d 7.96 (1H, d, J=8.1 Hz, 6-H), d 7.39-6.83 (13H, m, DMTr), d 6.10-5.73 (1H, m, CHF2-CH2-O), d 6.00 (1H, d, J=2.7 Hz, 1'-H), d 5.32-5.28 (1H, m, 5-H), d 5.07 (1H, d, J=6.9 Hz, H—C of acetal), d 4.93 (1H, d, J=6.6 Hz, H—C of acetal), d 4.53-4.47 (1H, m, 3'-H), d 4.34-4.31 (1H, m, 2'-H), d 4.08-4.06 (1H, m, 4'-H), d 3.88-3.78 (8H, m, CHCl2-CH2-O, MeO×2), d 3.60-3.51 (2H, m, 5'-H), d 2.39 (1H, d, 3'-OH).

2'-O-(2,2,2-trifluoro)ethoxymethyl-5'-O-(4,4'-dimethoxytrityl)uridine (4e)

2'-O-(2,2,2-trifluoro)ethoxymethyl-3',5'-O-(1,1,3,3-tetraisopropyldisiloxane-1,3diyl)uridine, the compound represented by Formula 2e (414 mg, 692 mmol, crude) was dissolved in methanol (4 ml) by performing azeotropic drying by pyridine and toluene. To this mixture, ammonium fluoride (103 mg, 2.78 mmol) was added, and the reaction mixture was stirred at 50° C. for 8 hours. The reaction mixture was concentrated under reduced pressure, and acetonitrile (15 ml) was added, and the insoluble matters were removed by filtration. This was washed with hexane (15 ml×2), and the collected washing liquid was extracted with acetonitrile (10 ml). The collected organic layer was concentrated under reduced pressure, and used in the next reaction without performing further purification. The crude purified matter was dissolved in pyridine (7 ml) by performing azeotropic drying by pyridine. To this mixture, DMTrCl (510 mg, 1.51 mmol) was added, and the reaction mixture was stirred at room temperature for 17 hours. The reaction was stopped with methanol (1 ml), and then the solvent was distilled away under reduced pressure, and chloroform (20 ml) was added. This was washed with saturated saline (20 ml×3), and the collected washing liquid was extracted with chloroform (20 ml). The collected organic layer was dried with anhydrous sodium sulfate, and then filtered, and dried and concentrated under reduced pressure, and the resultant was purified with silica gel chromatography [1×15 cm, 10 g of silica gel, dichloromethane-methanol-pyridine (99.5:0:0.5, v/v/v→98.5:1:0.5, v/v/v)], whereby to obtain a compound represented by Formula 4e (205 m, 19% yield from the compound represented by Formula 1).

1H NMR (300 MHz, CDCl3) d 8.06 (1H, br, NH), d 7.95 (1H, d, J=8.4 Hz, 6-H), d 7.39-6.84 (13H, m, DMTr), d 6.00 (1H, d, J=2.7 Hz, 1'-H), d 5.1 (1H, d, J=8.4 Hz, 5-H), d 5.10 (1H, d, J=6.9 Hz, H—C of acetal), d 4.96 (1H, d, J=7.2 Hz, H—C of acetal), d 4.48 (1H, m, 3'-H), d 4.35-4.33 (1H, m, 2'-H), d 4.08-3.95 (2H, m, CF3-CH2-O, 4'-H), d 3.80 (6H, s, MeOx2), d 3.57-3.53 (2H, m, 5'-H), d 2.33 (1H, d, 3'-OH).

$^{31}$P NMR (121 MHz, CDCl3) d 151.35, d 150.48

Preparation of 2'-O-haloalchoxymethyl-5'-dimethoxytrityl)uridine 3'-(2-cyano ethyl diisopropylphosphoramidite) (5a-e)

Scheme 3

[Chemical Formula 13]

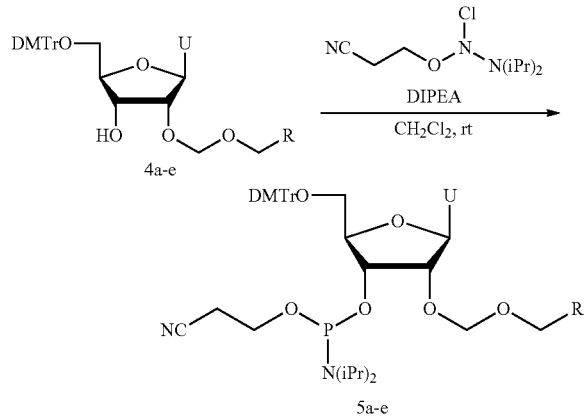

2a: R = CH$_2$Cl
2b: R = CHCl$_2$
2c: R = CCl$_3$
2d: R = CHF$_2$
2e: R = CF$_3$

In Scheme 3, DIPEA represents diisopropylamine.

2'-O-(2-chloro)ethoxymethyl-5'-O-(4,4'-dimethoxytrityl)uridine 3'-(2-cyanoethyl diisopropylphosphoramidite) (5a)

2'-O-2-chloroethoxymethyl-5'-O-(4,4'-dimethoxytrityl)uridine represented by Formula 4a (511 mg, 800 mmol) was dissolved in dichloromethane (4 ml) by performing azeotropic drying by pyridine and toluene. To this mixture, diisopropylamine (410 ml, 2.4 mmol) was added, and 2-cyanoethyldiisopropyl chlorophosphoramidite (268 ml, 1.2 mmol in 4 ml of CH$_2$Cl$_2$) was dropped. The reaction mixture was stirred at room temperature for 1 hour, and the reaction was stopped with ethanol (1.5 ml). To this mixture, dichloromethane (40 ml) was added, and the reaction mixture was washed with saturated sodium bicarbonate water (40 ml×3), and the collected washing liquid was extracted with dichloromethane (40 ml). The collected organic layer was dried with anhydrous sodium sulfate, and then filtered, and dried and concentrated under reduced pressure, and the resultant was purified with silica gel chromatography [2×10 cm, 15 g of amino silica gel, hexane-ethyl acetate (7:3, v/v→ethyl acetate only)], whereby to obtain a compound represented by Formula 5a as a diastereomer mixture of the target substance (469 mg, 70%).

1H NMR (300 MHz, CDCl3) d 9.15 (1H, br, NH), d 7.99-7.92 (1H, m, 6-H), d 7.41-6.84 (13H, m, DMTr), d 6.06 (1H, m, 1'-H), d 5.30-5.23 (1H, m, 5-H), d 5.06-4.93 (2H, m, H—C of acetal), d 4.58-4.56 (1H, m, 3'-H), d 4.47-4.42 (1H, m, 2'-H), d 4.27-4.18 (1H, m, 4'-H), d 3.99-3.44 (16H, m, MeOx 2,5'-H, 2×(CH3)2CH—N, CH2Cl—CH2-O, NC—CH2CH2—), d 2.69-2.41 (2H, m, NC—CH2CH2-), d 1.17-1.02 (12H, m, 2×(CH3)2CH—N).

2'-O-(2,2-dichloro)ethoxymethyl-5'-O-(4,4'-dimethoxytrityl)uridine 3'-(2-cyano ethyl diisopropylphosphoramidite) (5b)

2'-O-2,2-dichloroethoxymethyl-5'-O-(4,4'-dimethoxytrityl)uridine represented by Formula 4b was dissolved in dichloromethane (3 ml) by performing azeotropic drying by pyridine and toluene. To this mixture, diisopropylamine (255 ml, 1.5 mmol) was added, and 2-cyanoethyldiisopropyl chlorophosphoramidite (167 ml, 1.2 mmol in 2 ml of CH$_2$Cl$_2$) was dropped. The reaction mixture was stirred at room temperature for 1.5 hours, and the reaction was stopped with ethanol (1 ml). To this mixture, dichloromethane (30 ml) was added, and the reaction mixture was washed with saturated sodium bicarbonate water (30 ml×3), and the collected washing liquid was extracted with dichloromethane (30 ml). The collected organic layer was dried with anhydrous sodium sulfate, and then filtered, and dried and concentrated under reduced pressure, and the resultant was purified with silica gel chromatography [2×6 cm, 10 g of amino silica gel, hexane-ethyl acetate (7:3, v/v→ethyl acetate only)], whereby to obtain a compound represented by the Formula 5b as a diastereomer mixture of the target substance (324 mg, 77%).

1H NMR (300 MHz, CDCl3) d 8.16 (1H, br, NH), d 7.99-7.94 (1H, m, 6-H), d 7.41-6.84 (13H, m, DMTr), d 6.04-6.01 (1H, m, 1'-H), d 5.86-5.79 (1H, m, 5-H), d 5.29-5.20 (1H, m, CHCl2-CH2-O), d 5.02-4.86 (2H, m, H—C of acetal), d 4.58-4.54 (1H, m, 3'-H), d 4.44-4.41 (1H, m, 2'-H), d 4.27-4.18 (1H, m, 4'-H), d 4.13-3.42 (14H, m, MeOx2,5'-H, 2×(CH3)2CH—N, CHCl2-CH2-O, NC—CH2CH2-), d 2.68-2.44 (2H, m, NC—CH2CH2-), d 1.25-1.03 (12H, m, 2×(CH3)2CH—N).

31P NMR (121 MHz, CDCl3) d 151.49, d 150.43

2'-O-(2,2,2-trichloro)ethoxymethyl-5'-O-(4,4'-dimethoxytrityl)uridine 3'-(2-cyano ethyl diisopropylphosphoramidite) (5c)

2'-O-2,2,2-trichloroethoxymethyl-5'-O-(4,4'-dimethoxytrityl)uridine represented by Formula 4c (283 mg, 400 mmol) was dissolved in dichloromethane (2 ml) by performing azeotropic drying by pyridine and toluene. To this mixture, diisopropylamine (204 ml, 1.5 mmol) was added, and 2-cyanoethyldiisopropyl chlorophosphoramidite (134 ml, 600 mmol in 2 ml of CH$_2$Cl$_2$) was dropped. The reaction mixture was stirred at room temperature for 1 hour, and the reaction was stopped with ethanol (1 ml). To this mixture, dichloromethane (25 ml) was added, and the reaction mixture was washed with saturated sodium bicarbonate water (25 ml×3), and the collected washing liquid was extracted with dichloromethane (25 ml). The collected organic layer was dried with anhydrous sodium sulfate, and then filtered, and dried and concentrated under reduced pressure, and the resultant was purified with silica gel chromatography [2×6 cm, 10 g of amino silica gel, hexane-ethyl acetate (8:2, v/v→ethyl acetate only)], whereby to obtain a compound represented by Formula 5c as a diastereomer mixture of the target substance (285 mg, 83%).

1H NMR (300 MHz, CDCl3) d 8.11 (1H, br, NH), d 7.96-7.94 (1H, m, 6-H), d 7.41-6.84 (13H, m, DMTr), d 6.06 (1H, m, 1'-H), d 5.30-5.06 (3H, m, 5-H, H—C of acetal), d 4.59-4.47 (2H, m, 3'-H, 2'-H), d 4.29-3.41 (15H, m, 4'-H, MeOx 2,5'-H, 2×(CH3)2CH—N, CCl3-CH2-O, NC—CH2CH2-), d 2.68-2.42 (2H, m, NC—CH2CH2-), d 1.26-1.03 (12H, m, 2×(CH3)2CH—N).

31P NMR (121 MHz, CDCl3) d 151.49, d 150.43

2'-O-(2,2-difluoro)ethoxymethyl-5'-O-(4,4'-dimethoxytrityl)uridine 3'-(2-cyano ethyl diisopropylphosphoramidite) (5d)

2'-O-2,2-difluoroethoxymethyl-5'-O-(4,4'-dimethoxytrityl)uridine represented by Formula 4d (320 mg, 500 mmol) was dissolved in dichloromethane (5 ml) by performing azeotropic drying by pyridine and toluene. To this mixture, diisopropylamine (255 ml, 1.5 mmol) was added, and 2-cyanoethyldiisopropyl chlorophosphoramidite (225 ml, 1 mmol) was dropped under ice bath. The reaction mixture was stirred at room temperature for 1 hour, and chloroform (30 ml) was added to the reaction mixture. This was washed with phosphate buffer (pH 7.0, 20 ml×4), and the collected washing liquid was extracted with chloroform (40 ml). The collected organic layer was dried with anhydrous sodium sulfate, and then filtered, and dried and concentrated under reduced pressure, and the resultant was purified with silica gel chromatography [1×8 cm, 5 g of amino silica gel, hexane-ethyl acetate (7:3, v/v→ethyl acetate only)], whereby to obtain a compound represented by Formula 5d as a diastereomer mixture of the target substance (227 mg, 54%).

1H NMR (300 MHz, CDCl3) d 8.10 (1H, br, NH), d 8.00-7.94 (1H, m, 6-H), d 7.39-6.84 (13H, m, DMTr), d 6.10-5.73 (2H, m, 1'-H), d 5.28-5.20 (2H, m, CHF2-CH2-O, 5-H), d 5.03-4.89 (2H, m, H—C of acetal), d 4.61-4.56 (1H, m, 3'-H), d 4.43-4.41 (1H, m, 2'-H), d 4.27-4.20 (1H, m, 4'-H), d 3.93-3.42 (14H, m, MeO×2,5'-H, 2×(CH3)2CH—N, CHF2-CH2-O, NC—CH2CH2-), d 2.65-2.44 (2H, m, NC—CH2CH2-), d 1.29-0.85 (12H, m, 2×(CH3)2CH—N).

31P NMR (121 MHz, CDCl3) d 151.56, d 150.38

2'-O-(2,2,2-trifluoro)ethoxymethyl-5'-O-(4,4'-dimethoxytrityl)uridine 3'-(2-cyano ethyl diisopropylphosphoramidite) (5e)

2'-O-2,2,2-trifluoroethoxymethyl-5'-O-(4,4'-dimethoxytrityl)uridine represented by Formula 4e (184 mg, 280 mmol) was dissolved in dichloromethane (2 ml) by performing azeotropic drying by pyridine and toluene. To this mixture, diisopropylamine (143 ml, 840 mmol) was added, and 2-cyanoethyldiisopropyl chlorophosphoramidite (93.7 ml, 420 mmol in 1 ml of CH$_2$Cl$_2$) was dropped. The reaction mixture was stirred at room temperature for 1.5 hours, and the reaction was stopped with ethanol (500 ml). To this mixture, dichloromethane (15 ml) was added, and the reaction mixture was washed with saturated sodium bicarbonate water (15 ml×3), and the collected washing liquid was extracted with dichloromethane (15 ml). The collected organic layer was dried with anhydrous sodium sulfate, and then filtered, and dried and concentrated under reduced pressure, and the resultant was purified with silica gel chromatography [2×7 cm, 11 g of amino silica gel, hexane-ethyl acetate (8:2, v/v→ethyl acetate only)], whereby to obtain a compound represented by Formula 5e as a diastereomer mixture of the target substance (188 mg, 80%).

1H NMR (300 MHz, CDCl3) d 9.00 (1H, br, NH), d 7.99-7.94 (1H, m, 6-H), d 7.39-6.84 (13H, m, DMTr), d 6.01 (1H, m, 1'-H), d 5.30-5.21 (1H, m, 5-H), d 5.05-4.97 (2H, m, H—C of acetal), d 4.62-4.55 (1H, m, 3'-H), d 4.44 (1H, m, 2'-H), d 4.27-4.18 (1H, m, 4'-H), d 4.10-3.42 (14H, m, MeO×2,5'-H, 2×(CH3)2CH—N, CCl3-CH2-O, NC—CH2CH2-), d 2.64-2.41 (2H, m, NC—CH2CH2-), d 1.26-1.02 (12H, m, 2×(CH3)2CH—N).

31P NMR (121 MHz, CDCl3) d 151.74, d 150.40

Example 3

Preparation of 2'-O-(2-fluoro)ethoxymethyl-5'-O-(4,4'-dimethoxytrityl)uridine 3'-(2-cyanoethyl diisopropylphosphoramidite) (5f)

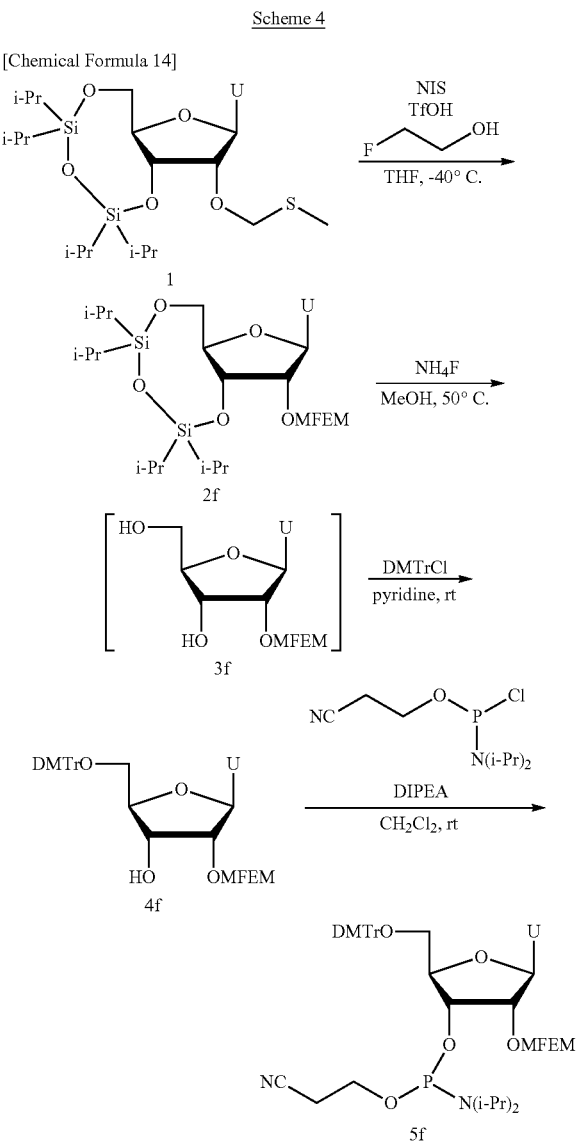

Scheme 4

[Chemical Formula 14]

In Scheme 4, NIS represents N-iodosuccinimide. TfOH represents trifluoromethane sulfonic acid. THF represents tetrahydrofuran. MeOH represents methanol. DMTrCl represents 4,4'-dimethoxytrityl chloride. Pyridine represents pyridine. The rt represents room temperature.

2'-O-(2-fluoro)ethoxymethyl-3',5'-O-(1,1,3,3-tetraisopropyldisiloxane-1,3-diyl)uridine (2f)

The crude purified matter of 2f was obtained by similar techniques to those of 2a from 1-(1.64 g, 3 mmol) and 2-fluoroethanol (1.65 ml, 30 mmol), Purification was performed with silica gel chromatography [3×17 cm, 50 g of silica gel, hexane-ethyl acetate (7:3, v/v)], to obtain 2f (1.13 g, 66%).

1H NMR (300 MHz, CDCl3), 9.57 (1H, br, NH), 7.90 (1H, d, J=8.1 Hz, 6-H), 5.76 (1H, s, 1'-H), 5.69 (1H, d, J=8.1 Hz, 5-H), 5.04 (1H, d, J=6.9 Hz, H—C of acetal), 5.00 (1H, d, J=6.9 Hz, H—C of acetal), 4.68-4.53 (2H, m, CH2F—CH2-O) 4.29-3.86 (7H, m, 2'-H, 3'-H, 4'-H, 5'-H, CH2F—CH2-O), 1.10-0.91 (28H, m, iPr×4).

2'-O-(2-fluoro)ethoxymethyl-5'-O-(4,4'-dimethoxytrityl)uridine (4f)

The crude purified matter of 4f was obtained by using 2'-O-(2-fluoro)ethoxymethyl-3',5'-O-(1,1,3,3-tetraisopropyldisiloxane-1,3-diyl)uridine 2f (1.13 g, 2.0 mmol) as a raw material by similar techniques to those of 4a. Purification was performed with silica gel chromatography [2.5×15 cm, 22 g of silica gel, dichloromethane-methanol-pyridine (99.5:0:0.5, v/v/v→96.5:1:0.5, v/v/v)] to obtain 4f (908 mg, 73%).

1H NMR (300 MHz, CDCl3) 8.03 (1H, br, NH), 7.93 (1H, d, J=8.4 Hz, 6-H), 7.39-6.82 (13H, m, DMTr), 6.02 (1H, d, J=3.3 Hz, 1'-H), 5.30-5.28 (1H, m, 5-H), 5.04 (1H, d, J=6.6 Hz, H—C of acetal), 4.93 (1H, d, J=6.6 Hz, H—C of acetal), 4.67-4.46 (3H, m, 3'-H, CH2F—CH2-O), 4.36-4.34 (1H, m, 2'-H), 4.10-4.08 (1H, m, 4'-H), 3.94-3.80 (8H, m, MeO×2, CH2F—CH2-O), 3.53-3.52 (2H, m, 5'-H), 2.61 (1H, d, 3'-OH).

2'-O-(2-fluoro)ethoxymethyl-5'-O-(4,4'-dimethoxytrityl)uridine 3'-(2-cyanoethyl diisopropylphosphoramidite) (5f)

The diastereomer mixture of 5f was obtained by being synthesized and purified similarly to 5a using 2'-O-(2-fluoro)ethoxymethyl-5'-O-(4,4'-dimethoxytrityl)uridine 4f (908 mg, 1.46 mmol) as a raw material (918 mg, 77%).

1H NMR (300 MHz, CDCl3) d 8.34 (1H, br, NH), d 7.95-7.90 (1H, m, 6-H), d 7.41-6.84 (13H, m, DMTr), d 6.06 (1H, m, 1'-H), d 5.30-5.23 (1H, m, 5-H), d 5.01-4.86 (2H, m, H—C of acetal), d 4.67-4.43 (4H, m, 2'-H, 3'-H, CH2F—CH2-O), d 3.97-3.40 (14H, m, MeO×2,5'-H, 2×(CH3)2CH—N, CH2F—CH2-O, NC—CH2CH2-), d 2.68-2.41 (2H, m, NC—CH2CH2-), d 1.28-1.03 (12H, m, 2×(CH3)2CH—N).

31P NMR (121 MHz, CDCl3) d 151.1, d 150.8

Example 4

Solid Phase Synthesis Using DNA Synthesizer ABI Expedite 8909

The chain length elongation cycle was performed by the protocol of 2'-O-TBDMS RNA 0.2 micromole scale. All of the reagents for synthesis were those for ABI purchased from Glen Research Corporation. For the solid phase carrier, U-RNA-CPG (0.2 micromole for Expedite) purchased from Glen Research Corporation was used. The amidite unit was used as dissolved in dichloromethane.

After synthesis, ammonia water (1 ml) was added with respect to the column filled with CPG, and the reaction mixture was reacted at room temperature for 3 hours. The solution was concentrated under reduced pressure, and dried by freeze-drying. This was dissolved in water, and analyzed and purified using reverse phase HPLC.

Protocol of RNA Synthesis (2'-O-TBDMS RNA 0.2 mmol Scale)

TABLE 1

| Function | Node | Amount/Arg1 | Time(sec)/Arg2 | Description |
|---|---|---|---|---|
| $Deblocking | | | | |
| 144 /*Index Fract. Coll. | */ NA | 1 | 0 | "Event out ON" |
| 0 /*Default | */ WAIT | 0 | 1.5 | "Wait" |
| 141 /*Trityl Mon. On/Off | */ NA | 1 | 1 | "START data collection" |
| 16 /*Dblk | */ PULSE | 10 | 0 | "Dblk to column" |
| 16 /*Dblk | */ PULSE | 50 | 60 | "Deblock" |
| 38 /*Diverted Wsh A | */ PULSE | 40 | 0 | "Flush system with Wsh A" |
| 141 /*Trityl Mon. On/Off | */ NA | 0 | 1 | "STOP data collection" |
| 144 /*Index Fract. Coll. | */ NA | 2 | 0 | "Event out OFF" |
| $Coupling | | | | |
| 1 /*Wsh | */ PULSE | 5 | 0 | "Flush system with Wsh" |
| 2 /*Act | */ PULSE | 5 | 0 | "Flush system with Act" |
| 18 /*A + Act | */ PULSE | 5 | 0 | "Monomer + Act to column" |
| 2 /*Act | */ PULSE | 1 | 0 | "Chase with Act" |
| 2 /*Act | */ PULSE | 4 | 400 | "Act" |
| 1 /*Wsh | */ PULSE | 2 | 350 | "Couple monomer" |
| 1 /*Wsh | */ PULSE | 13 | 0 | "Flush system with Wsh" |
| $Capping | | | | |
| 12 /*Wsh A | */ PULSE | 20 | 0 | "Flush system with Wsh A" |
| 13 /*Caps | */ PULSE | 8 | 0 | "Caps to column" |
| 12 /*Wsh A | */ PULSE | 6 | 15 | "Cap" |
| 12 /*Wsh A | */ PULSE | 14 | 0 | "Flush system with Wsh A" |
| $Oxidizing | | | | |
| 15 /*Ox | */ PULSE | 15 | 0 | "Ox to column" |
| 12 /*Wsh A | */ PULSE | 15 | 0 | "Flush system with Wsh B" |
| $Capping | | | | |
| 13 /*Caps | */ PULSE | 7 | 0 | "Caps to column" |
| 12 /*Wsh A | */ PULSE | 30 | 0 | "End of cycle wash" |

Sequence and Property of Synthesized Oligonucleotide

TABLE 2

| 2'-O-modifications | sequence (U:modified U) | calcd MW | found MW | yield |
|---|---|---|---|---|
| —O—CH$_2$—O—CH$_2$CH$_2$Cl | UUUUUUUUUUUU | 4622.4 | 4624.5 | 24% |
| —O—CH$_2$—O—CH$_2$CHCl$_2$ | UUUUUUUUUUUU | 4996.0 | 5006.9 | 52% |
| —O—CH$_2$—O—CH$_2$CCl$_3$ | UUUUUUUUUUUU | 5369.5 | 5358.3 | 28% |
| —O—CH$_2$—O—CH$_2$CHF$_2$ | UUUUUUUUUUUU | 4675.7 | 4688.5 | 42% |
| —O—CH$_2$—O—CH$_2$CF$_3$ | UUUUUUUUUUUU | 4842.5 | 4855.0 | 18% |
| —O—CH$_2$—O—CH$_2$CH$_2$F | UUUUUUUUUUUU | | | 15% |

The yield was obtained from ultraviolet absorption spectrum at 260 nm.

Analysis for Melting Temperature of U$_{12}$-A$_{12}$ Duplex

The synthesized U$_{12}$ oligomer and rA$_{12}$ or dA$_{12}$ oligomer of 0.3 nmol, respectively were dissolved in 150 ml of 10 mM phosphate-100 mM NaCl-0.1 mM EDTA buffer (pH 7.0). 100 ml of the oligomer solution was added to a 8-run cell, and the reaction mixture was temperature-increased to 90° C. at a speed of 5° C./min from room temperature, and then kept at 90° C. for 10 minutes. The reaction mixture was temperature-decreased to 0° C. at a speed of –2° C., and the annealing was performed. The oligomer solution was stood at 4° C. for 1 hour, and then the melting temperature T$_m$ value was measured. The oligomer solution was put into the cell, and deaerated under reduced pressure for 15 minutes, and then the absorbance was measured at 260 nm at an interval of 0.5° C. with temperature-increase to 90° C. at a speed of 0.5° C./min under nitrogen flow.

(1) Influence of Substituent on the Alkoxymethyl Skeleton Modification (Vs RNA U$_{12}$-rA$_{12}$)

The influence of the substituent on the alkoxymethyl skeleton modification was investigated. The results thereof are illustrated in FIG. 1. FIG. 1 is a graph, instead of a drawing, illustrating the influence of the substituent on the alkoxymethyl skeleton modification. In the figure, the vertical axis represents the relative absorption amount. U represents a nucleic acid of which the nucleic-acid base is uracil. DFEM represents 2,2-difluoroethoxymethyl-modified body of the nucleic acid. DCEM represents 2,2-dichloroethoxymethyl-modified body of the nucleic acid. EOM represents 2'-O-ethoxymethyl-modified body of the nucleic acid. In addition, these characteristics are listed in the Table below.

TABLE 3

| modification | T$_m$ (° C.) | ΔT$_m$ (° C.) | ΔT$_m$/modfication (° C.) |
|---|---|---|---|
| rU | 15.4 | | |
| EOM (—O—CH$_2$—O—CH$_2$CH$_3$) | 12.8 | –2.6 | –0.2 |
| DFEM (—O—CH$_2$—O—CH$_2$CHF$_2$) | 18.9 | +3.5 | +0.3 |
| DCEM (—O—CH$_2$—O—CH$_2$CHCl$_2$) | 26.2 | +10.8 | +1.0 |

From the Table, it was listed again that the double strand melting temperature T$_m$ decreases by modification of 2'-O-ethoxymethyl. On the other hand, it was listed that the double strand melting temperature T$_m$ increases by modification of halo-substituted 2'-O-ethoxymethyl. Particularly, it was listed that the 2,2-dichloroethoxymethyl-modified body has a very high double strand-binding ability.

(2) Influence of the Number of Substituents on Alkoxymethyl Skeleton Modification (2-1) Fluorine-Containing Modified Body (Vs RNA U$_{12}$-rA$_{12}$)

Figure 2:
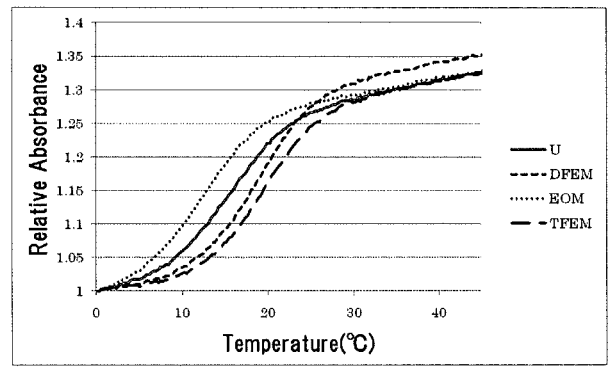
FIG. 2 is a graph, instead of a drawing, illustrating the influence of the number of substituents of a fluorine-containing modified body.

The influence of the number of the substituents of the fluorine-containing modified body was investigated. The results thereof are illustrated in FIG. 2. FIG. 2 is a graph, instead of a drawing, illustrating the influence of the number of the substituents of the fluorine-containing modified body. In the figure, the vertical axis represents the relative absorption amount. U represents a nucleic acid of which the nucleic-acid base is uracil. DFEM represents the 2,2-difluoroethoxymethyl-modified body of the nucleic acid. TFEM represents the 2,2,2-trichloroethoxymethyl-modified body of the nucleic acid. EOM represents the 2'-O-ethoxymethyl-modified body of the nucleic acid. In addition, these characteristics are listed in the Table below.

TABLE 4

| modification | T$_m$ (° C.) | ΔT$_m$ (° C.) | ΔT$_m$/modfication (° C.) |
|---|---|---|---|
| rU | 15.4 | | |
| EOM (—O—CH$_2$—O—CH$_2$CH$_3$) | 12.8 | –2.6 | –0.2 |

TABLE 4-continued

| modification | $T_m$ (° C.) | $\Delta T_m$ (° C.) | $\Delta T_m$/modfica- tion (° C.) |
|---|---|---|---|
| 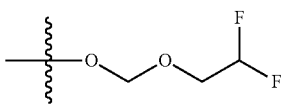 [SMILES: *OCOCC(F)F] DFEM | 18.9 | +3.5 | +0.3 |
| 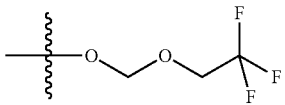 [SMILES: *OCOCC(F)(F)F] TFEM | 19.9 | +4.5 | +0.4 |

From the Table, it is understood that a ribonucleoside having, as a protective group, a haloethoxymethyl group which is substituted with a fluorine atom does not have so high double strand-forming ability.

(2-2) Modified Body Containing Chlorine (Vs RNA $U_{12}$-$rA_{12}$)

Figure 3:
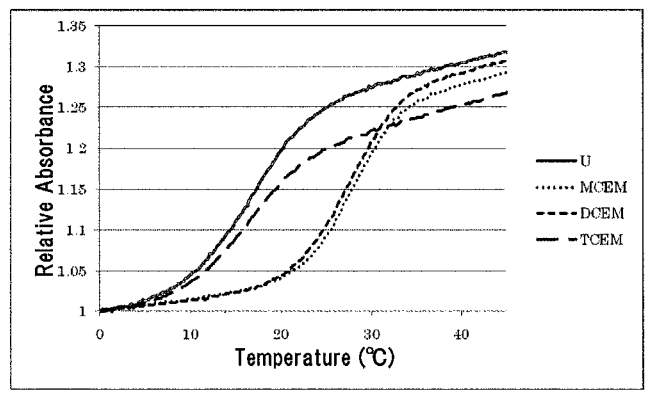
FIG. 3 is a graph, instead of a drawing, illustrating the influence of the number of substituents of a chlorine atom-containing modified body.

The melting temperature of the chlorine-containing modified body was measured. The results thereof are illustrated in FIG. 3. FIG. 3 is a graph, instead of a drawing, illustrating the influence of the number of the substituents of the chlorine atom-containing modified body.

TABLE 5

| modification | $T_m$ (° C.) | $\Delta T_m$ (° C.) | $\Delta T_m$/modfica- tion (° C.) |
|---|---|---|---|
| rU | 16.8 | | |
| 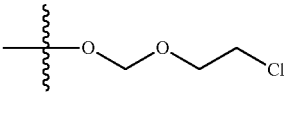 [SMILES: *OCOCCCl] MCEM | 27.9 | +11.1 | +1.0 |
| 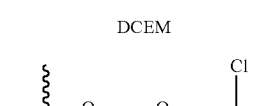 DCEM | 27.6 | +10.8 | +1.0 |
| 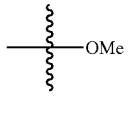 TCEM | 16.9 | +0.1 | — |

From the Table, it is understood that the melting temperature increases very prominently in the chlorine atom-mono-substituted and disubstituted bodies.

(3) Comparison of Haloalkoxymethyl-Modified Body with CEM Body and Me Body (Vs RNA $U_{12}$-$rA_{12}$)

Figure 4:
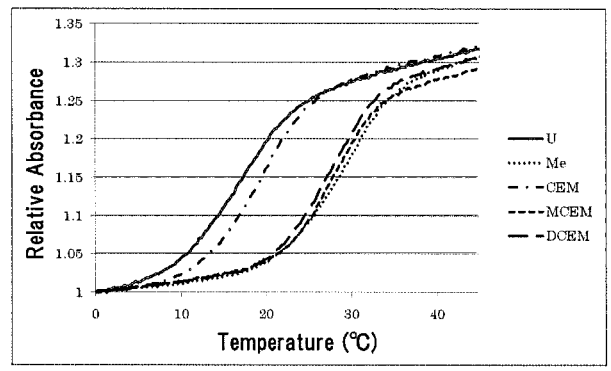
FIG. 4 is a graph, instead of a drawing, illustrating the comparison of chlorine atom-monosubstituted and disubstituted bodies with a cyano group-substituted body and a methyl-substituted body.

Next, as described above, the chlorine atom-monosubstituted and disubstituted bodies showing the prominent melting temperature were compared with the 2-cyanoethoxymethyl (CEM)-substituted body and the methyl-substituted body. The results thereof are illustrated in FIG. 4. FIG. 4 is a graph, instead of a drawing, that shows comparison of the chlorine atom-monosubstituted and disubstituted bodies with the cyano group-substituted body and the methyl-substituted body.

TABLE 6

| modification | $T_m$ (° C.) | $\Delta T_m$ (° C.) | $\Delta T_m$/modfica- tion (° C.) |
|---|---|---|---|
| rU | 16.8 | | |
| 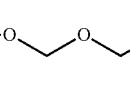 —OMe | 28.9 | +12.1 | +1.1 |
| 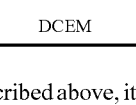 CEM | 19.6 | +2.8 | +0.3 |
| 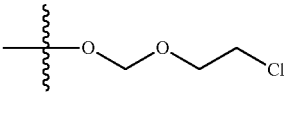 [SMILES: *OCOCCCl] MCEM | 27.9 | +11.1 | +1.0 |
| 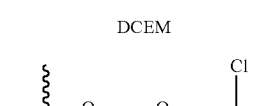 DCEM | 27.6 | +10.8 | +1.0 |

As described above, it is understood that the chlorine atom-monosubstituted and disubstituted bodies showed dominant increase of the melting temperature in comparison to the 2-cyanoethoxymethyl (CEM) substituted body. In addition, it is understood that the chlorine atom-monosubstituted and disubstituted bodies show high melting temperature in a comparable level to the methyl-substituted body.

(4) Investigation of Affinity with Respect to DNA (4-1) Fluorine-Containing Modified Body (Vs DNA $U_{12}$-$dA_{12}$)

Figure 5:
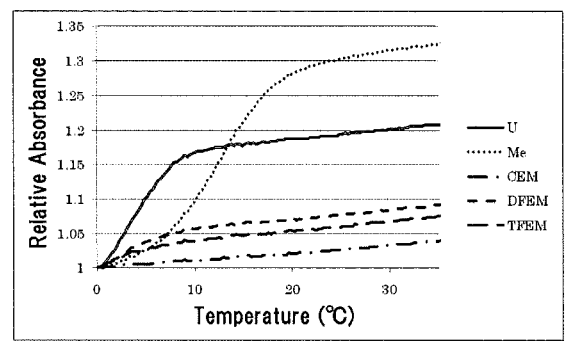
FIG. 5 is a graph, instead of a drawing, illustrating the affinity of the fluorine-containing modified body with respect to DNA.

Next, the affinity of the fluorine-containing modified body with respect to DNA was investigated. The results thereof are illustrated in FIG. 5. FIG. 5 is a graph, instead of a drawing, illustrating the affinity of the fluorine-containing modified body with respect to DNA.

TABLE 7

| modification | $T_m$ (° C.) | $\Delta T_m$ (° C.) | $\Delta T_m$/modfica- tion (° C.) |
|---|---|---|---|
| rU | 6.3 | | |
| 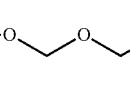 —OMe | 13.3 | +6.0 | +0.6 |
| 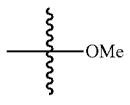 CEM | — | — | — |

TABLE 7-continued

| modification | $T_m$ (°C.) | $\Delta T_m$ (°C.) | $\Delta T_m$/modfica- tion (°C.) |
|---|---|---|---|
| DFEM | — | — | — |
| TFEM | — | — | — |

The fluorine atom-containing modified body showed no affinity with respect to DNA.

(4-2) Chlorine-Containing Modified Body (Vs DNA $U_{12}$-$dA_{12}$)

Figure 6:
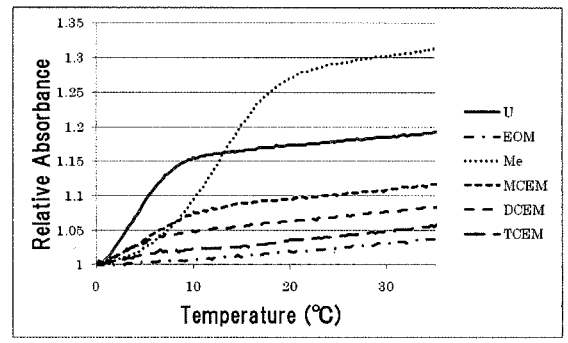
FIG. 6 is a graph, instead of a drawing, illustrating the affinity of the chlorine atom-containing modified body with respect to DNA.

Next, the affinity of the chlorine-containing modified body with respect to DNA was investigated. The results thereof are illustrated in FIG. 6. FIG. 6 is a graph, instead of a drawing, illustrating the affinity of the chlorine atom-containing modified body with respect to DNA.

TABLE 8

| modification | $T_m$ (°C.) | $\Delta T_m$ (°C.) | $\Delta T_m$/modifica- tion (°C.) |
|---|---|---|---|
| rU | 5.1 | | |
| EOM | — | — | — |
| OMe | 12.8 | +7.7 | +0.7 |
| MCEM | — | — | — |
| DCEM | — | — | — |
| TCEM | — | — | — |

The chlorine atom-containing modified body showed no affinity with respect to DNA.

(5) Influence of Fluorine Substituent on Alkoxymethyl Skeleton Modification (Vs RNA $U_{12}$-$rA_{12}$)

Figure 7:
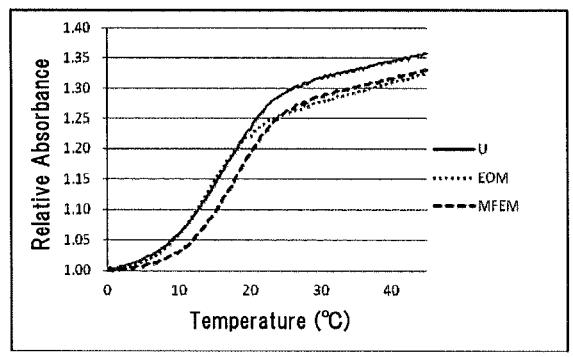
FIG. 7 is a graph, instead of a drawing, illustrating the influence of a substituent of the fluorine-containing modified body.

The influence of the substituent of the fluorine-containing modified body was investigated. The results thereof are illustrated in FIG. 7. FIG. 7 is a graph, instead of a drawing, illustrating the influence of the substituent of the fluorine-containing modified body. In the figure, the vertical axis represents the relative absorption amount. U represents a nucleic acid of which the nucleic-acid base is uracil. EOM represents the 2'-O-ethoxymethyl-modified body of the nucleic acid. MFEM represents the 2'-O-fluoroethoxymethyl-modified body of the nucleic acid. In addition, these characteristics are listed in the Table below.

TABLE 9

| modification | $T_m$ (°C.) | $\Delta T_m$ (°C.) | $\Delta T_m$/modifica- tion (°C.) |
|---|---|---|---|
| rU | 16.1 | | |
| EOM | 13.9 | −2.2 | −0.2 |
| MFEM | 17.3 | +1.2 | +0.1 |

From the Table, the ribonucleoside having a haloethoxymethyl group substituted with a fluorine atom has a higher double strand-forming ability than natural type RNA, but did not have so great effect of the stabilization.

INDUSTRIAL APPLICABILITY

An oligo ribonucleic acid (oligo RNA) draws attentions as a functional molecule that becomes a material for a pharmaceutical product such as antisense RNA, siRNA and an aptamer, and under development worldwide as a pharmaceutical product. Accordingly, the invention can be used in the field of the pharmaceutical industry.

The invention claimed is:

1. A ribonucleoside, a ribonucleotide, or a derivative thereof having a protective group at the 2'-position, wherein the protective group is represented by the following Formula (I):

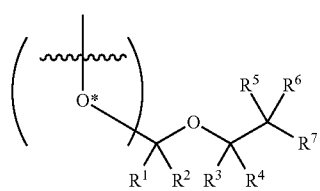

(I)

wherein O* represents an oxygen atom of the hydroxyl group at the 2' position of the ribonucleoside, the ribonucleotide, or the derivative thereof, $R^1$ and $R^2$ each represents a hydrogen atom, R³ and R⁴ may be identical or different, and each represents a hydrogen atom, a halogen atom, a $C_{1-3}$ alkyl group, a $C_{2-3}$ alkenyl group, a $C_{2-3}$ alkynyl group, a hydroxy $C_{2-3}$ alkyl group, or a $C_{1-3}$ haloalkyl group, R⁵ and R⁶ may be identical or different, and each represents a hydrogen atom, a halogen atom, a $C_{1-3}$ alkyl group, a $C_{2-3}$ alkenyl group, a $C_{2-3}$ alkynyl group, a hydroxy $C_{2-3}$ alkyl group, a $C_{1-3}$ haloalkyl group, a $C_{1-3}$ alkyl group substituted with one or two $C_{6-12}$ aryl groups, or a $C_{6-12}$ aryl group optionally having a substituent, and R⁷ represents a halogen atom or a $C_{1-3}$ haloalkyl group, wherein the derivative thereof is the ribonucleoside or the ribonucleotide having a 2-cyanoethyldiisopropyl phosphoramidite protecting group at the 3' position and/or a 4,4'-dimethoxytrityl group at the 5' position, or having a 1,1,3,3-tetraisopropyldisiloxane-1,3diyl protecting group attached to both the 3' position and the 5' position to form a cyclic structure.

2. The ribonucleoside, the ribonucleotide, or the derivative thereof having a protective group at the 2'-position according to claim 1,
wherein R³ and R⁴ may be identical or different, and each represents a hydrogen atom, a methyl group or an ethyl group,
R⁵ and R⁶ may be identical or different, and each represents a hydrogen atom, a halogen atom, or a $C_{1-3}$ haloalkyl group, and
R⁷ represents a halogen atom.

3. The ribonucleoside, the ribonucleotide, or the derivative thereof having a protective group at the 2'-position according to claim 1,
wherein all of R¹ to R⁴ represent a hydrogen atom,
R⁵ and R⁶ may be identical or different, and each represents a hydrogen atom, a fluorine atom, a chlorine atom or a bromine atom, and
R⁷ represents a fluorine atom, a chlorine atom or a bromine atom.

4. The ribonucleoside, the ribonucleotide, or the derivative thereof having a protective group at the 2'-position according to claim 1,
wherein all of R¹ to R⁵ represent a hydrogen atom,
R⁶ represents a hydrogen atom, a fluorine atom or a chlorine atom, and
R⁷ represents a fluorine atom or a chlorine atom.

5. The ribonucleoside, the ribonucleotide, or the derivative thereof having a protective group at the 2'-position according to claim 1,
wherein all of R¹ to R⁵ represent a hydrogen atom,
R⁶ represents a hydrogen atom, or a chlorine atom, and
R⁷ represents a chlorine atom.

6. The ribonucleoside, the ribonucleotide, or the derivative thereof having a protective group at the 2'-position according to claim 1, which is
2'-O-(2-chloro)ethoxymethyl-3',5'-O-(1,1,3,3-tetraisopropyldisiloxane-1,3diyl) nucleic acid base B,
2'-O-(2,2-dichloro)ethoxymethyl-3',5'-O-(1,1,3,3-tetraisopropyldisiloxane-1,3diyl) nucleic acid base B,
2'-O-(2,2,2-trichloro)ethoxymethyl-3',5'-O-(1,1,3,3-tetraisopropyldisiloxane-1,3diyl) nucleic acid base B,
2'-O-(2,2-difluoro)ethoxymethyl-3',5'-O-(1,1,3,3-tetraisopropyldisiloxane-1,3diyl) nucleic acid base B,
2'-O-(2,2,2-trifluoro)ethoxymethyl-3',5'-O-(1,1,3,3-tetraisopropyldisiloxane-1,3diyl) nucleic acid base B,
2'-O-(2-chloro)ethoxymethyl-5'-O-(4,4'-dimethoxytrityl) nucleic acid base B,
2'-O-(2,2-dichloro)ethoxymethyl-5'-O-(4,4'-dimethoxytrityl) nucleic acid base B,
2'-O-2,2,2-trichloroethoxymethyl-5'-O-(4,4'-dimethoxytrityl) nucleic acid base B,
2'-O-2,2-difluoroethoxymethyl-5'-O-(4,4'-dimethoxytrityl) nucleic acid base B,
2'-O-2,2,2-trifluoroethoxymethyl-5'-O-(4,4'-dimethoxytrityl) nucleic acid base B,
2'-O-(2-chloro)ethoxymethyl-5'-O-(4,4'-dimethoxytrityl) nucleic acid base B 3'-(2-cyanoethyldiisopropyl phosphoramidite),
2'-O-(2,2-dichloro)ethoxymethyl-5'-O-(4,4'-dimethoxytrityl) nucleic acid base B 3'-(2-cyanoethyldiisopropyl phosphoramidite),
2'-O-(2,2,2-trichloro)ethoxymethyl-5'-O-(4,4'-dimethoxytrityl) nucleic acid base B 3'-(2-cyanoethyldiisopropyl phosphoramidite),
2'-O-(2,2-difluoro)ethoxymethyl-5'-O-(4,4'-dimethoxytrityl) nucleic acid base B 3'-(2-cyanoethyldiisopropyl phosphoramidite),
2'-O-(2,2,2-trifluoro)ethoxymethyl-5'-O-(4,4'-dimethoxytrityl) nucleic acid base B 3'-(2-cyanoethyldiisopropyl phosphoramidite),
2'-O-(2-bromo)ethoxymethyl-3',5'-O-(1,1,3,3-tetraisopropyldisiloxane-1,3diyl) nucleic acid base B,
2-O-(2,2-dibromo)ethoxymethyl-3',5'-O-(1,1,3,3-tetraisopropyldi siloxane-1,3 diyl) nucleic acid base B,
2'-O-(2,2,2-tribromo)ethoxymethyl-3',5'-O-(1,1,3,3-tetraisopropyldisiloxane-1,3 diyl) nucleic acid base B,
2'-O-(2-bromo)ethoxymethyl-5'-O-(4,4'-dimethoxytrityl) nucleic acid base B 3'-(2-cyanoethyldiisopropyl phosphoramidite),
2'-O-(2,2-dibromo)ethoxymethyl-5'-O-(4,4'-dimethoxytrityl) nucleic acid base B 3'-(2-cyanoethyldiisopropyl phosphoramidite), or
2'-O-(2,2,2-tribromo)ethoxymethyl-5'-O-(4,4'-dimethoxytrityl) nucleic acid base B 3'-(2-cyanoethyldiisopropyl phosphoramidite),
wherein the nucleic acid base B is adenosine, guanosine, cytidine or uridine.

7. The ribonucleoside, the ribonucleotide, or the derivative thereof having a protective group at the 2'-position according to claim 1, which is
2'-O-(2-chloro)ethoxymethyl-5'-O-(4,4'-dimethoxytrityl) nucleic acid base B 3'-(2-cyanoethyldiisopropyl phosphoramidite), or
2'-O-(2,2-dichloro)ethoxymethyl-5'-O-(4,4'-dimethoxytrityl) nucleic acid base B 3'-(2-cyanoethyldiisopropyl phosphoramidite);
wherein the nucleic acid base B is adenosine, guanosine, cytidine or uridine.

8. A method of manufacturing the ribonucleoside, the ribonucleotide, or the derivative thereof represented by the Formula (I) according to claim 1, the method comprising:
reacting a compound represented by the following Formula (III) with a compound represented by the following Formula (II);

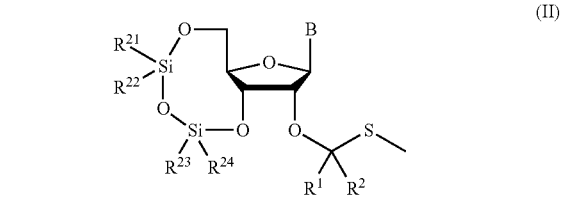

wherein in Formula (II), B represents a nucleic acid base that may be protected with a protective group, $R^{21}$, $R^{22}$, $R^{23}$ and $R^{24}$ may be identical or different, and each represents a alkyl group, a $C_{1-5}$ alkoxy group or a $C_{1-5}$ haloalkyl group that may be straight or branched, and $R^1$ and $R^2$ are each a hydrogen,

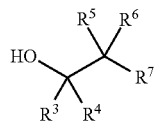
(III)

in Formula (III), $R^3$ to $R^7$ represent the same as $R^3$ to $R^7$ in Formula (I).

9. The method according to claim 8, wherein the reacting the compound represented by Formula (III) with the compound represented by Formula (II) produces a compound represented following Formula (IV), the method further comprising:
reacting the compound represented by Formula (IV) with a $C_{1-3}$ alcohol to obtain a compound represented by the following Formula (V); and
reacting the compound represented by Formula (V) with dimethoxytriphenylmethyl halide, to obtain a compound represented by Formula (VI).

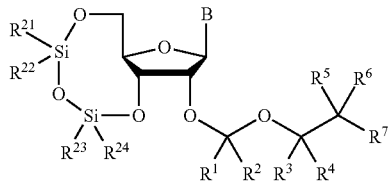
(IV)

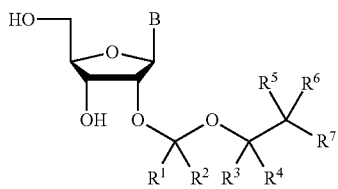
(V)

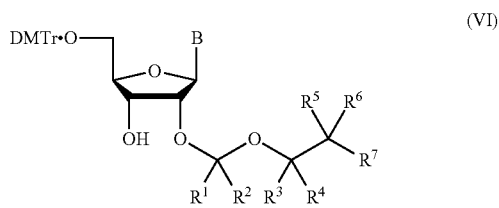
(VI)

10. The method according to claim 9, further comprising, after obtaining the compound represented by Formula (VI):
reacting the compound represented by Formula (VI) with a compound represented by the following Formula (VII) to obtain a compound represented by the following Formula (VIII);

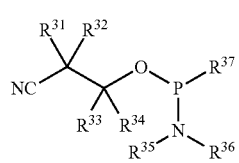
(VII)

in Formula (VII),
$R^{31}$ to $R^{34}$ may be identical or different, and each represents a hydrogen atom, a $C_{1-3}$ alkyl group, or a $C_{1-3}$ haloalkyl group,
$R^{35}$ and $R^{36}$ may be identical or different, and each represents a $C_{1-5}$ alkyl group or a $C_{1-5}$ haloalkyl group, and
$R^{37}$ represents a halogen atom;

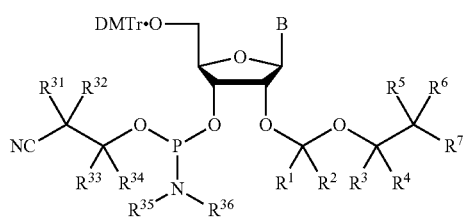
(VIII)

in Formula (VIII), B represents a nucleic acid base that may be protected with a protective group, $R^1$ to $R^7$ represent the same as $R^1$ to $R^7$ in Formula (I), $R^{31}$ to $R^{36}$ represent the same as $R^{31}$ to $R^{36}$ in Formula (VII), and the formula DMTr represents a 4,4'-dimethoxytrityl group.

* * * * *